(12) United States Patent
Timm et al.

(10) Patent No.: US 8,623,044 B2
(45) Date of Patent: Jan. 7, 2014

(54) CABLE ACTUATED END-EFFECTOR FOR A SURGICAL INSTRUMENT

(75) Inventors: Richard W. Timm, Cincinnati, OH (US); Suzanne E. Thompson, West Chester, OH (US); John V. Hunt, Cincinnati, OH (US); Gavin M. Monson, Oxford, OH (US); Omar J. Vakharia, Cincinnati, OH (US); Robert J. Laird, Morrow, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 645 days.

(21) Appl. No.: 12/758,284

(22) Filed: Apr. 12, 2010

(65) Prior Publication Data
US 2011/0251608 A1    Oct. 13, 2011

(51) Int. Cl.
*A61B 17/00* (2006.01)
*A61B 18/12* (2006.01)

(52) U.S. Cl.
USPC ............... 606/205; 606/45; 606/51; 606/207

(58) Field of Classification Search
USPC ............................. 606/45, 50–52, 205–207
See application file for complete search history.

(56) References Cited

U.S. PATENT DOCUMENTS

| | | |
|---|---|---|
| 3,580,841 A | 5/1971 | Cadotte et al. |
| 3,703,651 A | 11/1972 | Blowers |
| 4,058,126 A | 11/1977 | Leveen |
| 4,237,441 A | 12/1980 | van Konynenburg et al. |
| 4,304,987 A | 12/1981 | van Konynenburg |
| 4,545,926 A | 10/1985 | Fouts, Jr. et al. |
| 4,849,133 A | 7/1989 | Yoshida et al. |
| 4,910,389 A | 3/1990 | Sherman et al. |
| 5,104,025 A | 4/1992 | Main et al. |
| 5,106,538 A | 4/1992 | Barma et al. |
| 5,108,383 A | 4/1992 | White |
| 5,176,695 A | 1/1993 | Dulebohn |
| 5,205,459 A | 4/1993 | Brinkerhoff et al. |
| 5,282,800 A | 2/1994 | Foshee et al. |
| 5,285,945 A | 2/1994 | Brinkerhoff et al. |
| 5,309,927 A | 5/1994 | Welch |

(Continued)

FOREIGN PATENT DOCUMENTS

| | | |
|---|---|---|
| WO | WO 03/001986 A2 | 1/2003 |
| WO | WO 03/030708 A2 | 4/2003 |
| WO | WO 2005/052959 A2 | 6/2005 |

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

(Continued)

*Primary Examiner* — Michael Peffley

(57) ABSTRACT

Various embodiments are directed to a surgical instrument comprising a handle, a shaft coupled to the handle and extending along a longitudinal axis, an end effector, and a cable. The end effector may comprise a first jaw member, a second jaw member and a reciprocating member. The cable may extend distally from the handle through the shaft to a first pulley of the first jaw member. From the first pulley, the cable may extend proximally to the reciprocating member, such that proximally directed motion of the cable exerts a distally directed force on the reciprocating member.

21 Claims, 34 Drawing Sheets

(56) References Cited

U.S. PATENT DOCUMENTS

| | | | |
|---|---|---|---|
| 5,387,207 A | 2/1995 | Dyer et al. |
| 5,395,364 A | 3/1995 | Anderhub et al. |
| 5,403,312 A | 4/1995 | Yates et al. |
| 5,428,504 A | 6/1995 | Bhatla |
| 5,504,650 A | 4/1996 | Katsui et al. |
| 5,511,556 A | 4/1996 | DeSantis |
| 5,558,671 A | 9/1996 | Yates |
| 5,563,179 A | 10/1996 | Stone et al. |
| 5,599,350 A | 2/1997 | Schulze et al. |
| 5,624,452 A | 4/1997 | Yates |
| 5,647,871 A | 7/1997 | Levine et al. |
| 5,653,713 A | 8/1997 | Michelson |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,716,366 A | 2/1998 | Yates |
| 5,735,848 A | 4/1998 | Yates et al. |
| 5,755,717 A | 5/1998 | Yates et al. |
| 5,762,255 A | 6/1998 | Chrisman et al. |
| 5,807,393 A | 9/1998 | Williamson, IV et al. |
| 5,810,811 A | 9/1998 | Yates et al. |
| 5,817,033 A | 10/1998 | DeSantis et al. |
| 5,817,093 A | 10/1998 | Williamson, IV et al. |
| 5,880,668 A | 3/1999 | Hall |
| 6,003,517 A | 12/1999 | Sheffield et al. |
| 6,063,098 A | 5/2000 | Houser et al. |
| 6,074,389 A | 6/2000 | Levine et al. |
| 6,292,700 B1 | 9/2001 | Morrison et al. |
| 6,340,878 B1 | 1/2002 | Oglesbee |
| 6,500,176 B1 * | 12/2002 | Truckai et al. ............... 606/51 |
| 6,503,248 B1 | 1/2003 | Levine |
| 6,533,784 B2 | 3/2003 | Truckai et al. |
| 6,575,969 B1 | 6/2003 | Rittman, III et al. |
| 6,589,200 B1 | 7/2003 | Schwemberger et al. |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,770,072 B1 | 8/2004 | Truckai et al. |
| 6,773,409 B2 | 8/2004 | Truckai et al. |
| 6,789,939 B2 | 9/2004 | Schrödinger et al. |
| 6,802,843 B2 | 10/2004 | Truckai et al. |
| 6,811,842 B1 | 11/2004 | Ehrnsperger et al. |
| 6,840,938 B1 * | 1/2005 | Morley et al. ............... 606/51 |
| 6,905,497 B2 | 6/2005 | Truckai et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,070,597 B2 | 7/2006 | Truckai et al. |
| 7,083,619 B2 | 8/2006 | Truckai et al. |
| 7,087,054 B2 | 8/2006 | Truckai et al. |
| 7,112,201 B2 | 9/2006 | Truckai et al. |
| 7,125,409 B2 | 10/2006 | Truckai et al. |
| 7,143,925 B2 | 12/2006 | Shelton, IV et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,225,964 B2 | 6/2007 | Mastri et al. |
| 7,235,073 B2 | 6/2007 | Levine et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,371,227 B2 | 5/2008 | Zeiner |
| 7,381,209 B2 | 6/2008 | Truckai et al. |
| 7,404,508 B2 | 7/2008 | Smith et al. |
| 7,435,582 B2 | 10/2008 | Zimmermann et al. |
| 7,445,621 B2 | 11/2008 | Dumbauld et al. |
| 7,464,846 B2 | 12/2008 | Shelton, IV et al. |
| 7,510,107 B2 | 3/2009 | Timm et al. |
| 7,513,025 B2 | 4/2009 | Fischer |
| 7,550,216 B2 | 6/2009 | Ofer et al. |
| 7,588,176 B2 | 9/2009 | Timm et al. |
| 7,641,671 B2 | 1/2010 | Crainich |
| 7,665,647 B2 | 2/2010 | Shelton, IV et al. |
| 7,708,751 B2 | 5/2010 | Hughes et al. |
| 7,753,904 B2 | 7/2010 | Shelton, IV et al. |
| 7,766,910 B2 | 8/2010 | Hixson et al. |
| 7,784,663 B2 | 8/2010 | Shelton, IV |
| 7,819,298 B2 | 10/2010 | Hall et al. |
| 7,832,612 B2 | 11/2010 | Baxter, III et al. |
| 7,879,070 B2 | 2/2011 | Ortiz et al. |
| 8,246,618 B2 | 8/2012 | Bucciaglia et al. |
| 8,496,682 B2 | 7/2013 | Guerra et al. |
| 2004/0097919 A1 | 5/2004 | Wellman et al. |
| 2004/0232196 A1 | 11/2004 | Shelton, IV et al. |
| 2005/0090817 A1 | 4/2005 | Phan |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2007/0027469 A1 | 2/2007 | Smith et al. |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0191713 A1 | 8/2007 | Eichmann et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0239025 A1 | 10/2007 | Wiener et al. |
| 2008/0147062 A1 | 6/2008 | Truckai et al. |
| 2008/0167522 A1 | 7/2008 | Giordano et al. |
| 2008/0188851 A1 | 8/2008 | Truckai et al. |
| 2009/0030437 A1 | 1/2009 | Houser et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0206140 A1 | 8/2009 | Scheib et al. |
| 2009/0209979 A1 | 8/2009 | Yates et al. |
| 2009/0326530 A1 * | 12/2009 | Orban et al. ............... 606/51 |
| 2010/0010299 A1 | 1/2010 | Bakos et al. |
| 2010/0032470 A1 | 2/2010 | Hess et al. |
| 2010/0036370 A1 | 2/2010 | Mirel et al. |
| 2010/0036405 A1 | 2/2010 | Giordano et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0237132 A1 | 9/2010 | Measamer et al. |
| 2010/0264194 A1 | 10/2010 | Huang et al. |
| 2011/0251609 A1 | 10/2011 | Johnson et al. |
| 2011/0251612 A1 | 10/2011 | Faller et al. |
| 2011/0288452 A1 | 11/2011 | Houser et al. |

OTHER PUBLICATIONS

Hörmann et al., "Reversible and irreversible denaturation of collagen fibers." Biochemistry, 10, pp. 932-937 (1971).

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-induced changes in the mechanics of a collagenous tissue: pseudoelastic behavior at 37° C.," Journal of Biomechanics, 31, pp. 211-216 (1998).

Chen et al., "Heat-Induced Changes in the Mechanics of a Collagenous Tissue: Isothermal Free Shrinkage," Transactions of the ASME, vol. 119, pp. 372-378 (Nov. 1997).

(56) References Cited

OTHER PUBLICATIONS

Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1..., accessed Aug. 25, 2009.
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
Kurt Gieck & Reiner Gieck, Engineering Formulas §Z.7 (7th ed. 1997).
National Semiconductors Temperature Sensor Handbook—http://www.national.com/appinfo/tempsensors/files/temphb.pdf; accessed online: Apr. 1, 2011.
Glaser and Subak-Sharpe, *Integrated Circuit Engineering*, Addison-Wesley Publishing, Reading, MA (1979). (book—not attached).
U.S. Appl. No. 12/576,756, filed Oct. 9, 2009.
U.S. Appl. No. 12/576,776, filed Oct. 9, 2009.
U.S. Appl. No. 12/576,789, filed Oct. 9, 2009.
U.S. Appl. No. 12/576,808, filed Oct. 9, 2009.
U.S. Appl. No. 12/576,831, filed Oct. 9, 2009.
U.S. Appl. No. 12/836,366, filed Jul. 14, 2010.
U.S. Appl. No. 12/836,383, filed Jul. 14, 2010.
U.S. Appl. No. 12/836,396, filed Jul. 14, 2010.
U.S. Appl. No. 12/842,464, filed Jul. 23, 2010.
U.S. Appl. No. 12/842,476, filed Jul. 23, 2010.
U.S. Appl. No. 12/842,507, filed Jul. 23, 2010.
U.S. Appl. No. 12/842,518, filed Jul. 23, 2010.
U.S. Appl. No. 12/842,538, filed Jul. 23, 2010.
U.S. Appl. No. 12/842,565, filed Jul. 23, 2010.
U.S. Appl. No. 12/758,253, filed Apr. 12, 2010.
U.S. Appl. No. 12/758,268, filed Apr. 12, 2010.
U.S. Appl. No. 12/758,298, filed Apr. 12, 2010.
U.S. Appl. No. 12/765,175, filed Apr. 22, 2010.
U.S. Appl. No. 12/911,943, filed Oct. 26, 2010.
U.S. Appl. No. 12/841,480, filed Jul. 22, 2010.
U.S. Appl. No. 12/963,001, filed Dec. 8, 2010.
U.S. Appl. No. 12/732,992, filed Mar. 26, 2010.
U.S. Appl. No. 12/797,207, filed Jun. 9, 2010.
U.S. Appl. No. 12/797,252, filed Jun. 9, 2010.
U.S. Appl. No. 12/797,288, filed Jun. 9, 2010.
U.S. Appl. No. 12/797,305, filed Jun. 9, 2010.
U.S. Appl. No. 12/841,370, filed Jul. 22, 2010.
U.S. Appl. No. 12/797,844, filed Jun. 10, 2010.
U.S. Appl. No. 12/797,853, filed Jun. 10, 2010.
U.S. Appl. No. 12/797,861, filed Jun. 10, 2010.
U.S. Appl. No. 12/797,866, filed Jun. 10, 2010.
U.S. Appl. No. 12/832,345, filed Jul. 8, 2010.
U.S. Appl. No. 12/832,361, filed Jul. 8, 2010.
U.S. Appl. No. 12/781,243, filed May 17, 2010.
U.S. Appl. No. 12/775,724, filed May 7, 2010.
U.S. Appl. No. 12/622,113, filed Nov. 19, 2009.
U.S. Appl. No. 12/635,415, filed Dec. 10, 2009.
U.S. Appl. No. 12/647,134, filed Dec. 24, 2009.
International Search Report for PCT/US2011/031152, Jul. 27, 2011 (4 pages).
Written Opinion for PCT/US2011/031152, Jul. 27, 2011 (7 pages).

\* cited by examiner

CABLE ACTUATED END-EFFECTOR FOR A SURGICAL INSTRUMENT

BACKGROUND

Various embodiments are directed to cable actuated end effectors for surgical instruments and surgical instruments having cable-actuated end effectors.

Minimally invasive procedures are desirable because such procedures can reduce pain and provide relatively quick recovery times as compared to conventional open medical procedures. Many minimally invasive procedures are performed with an endoscope (including without limitation laparoscopes). Such procedures permit a physician to position, manipulate, and view medical instruments and accessories inside the patient through a small access opening in the patient's body. Laparoscopy is a term used to describe such an "endosurgical" approach using an endoscope (often a rigid laparoscope). In this type of procedure, accessory devices (such as end effectors for creating energy-induced tissue welds) are inserted into a patient through trocars placed through the body wall. Still less invasive treatments include those that are performed through insertion of an endoscope through a natural body orifice to a treatment region. Examples of this approach include, but are not limited to, cystoscopy, hysteroscopy, esophagogastroduodenoscopy, and colonoscopy.

Many of these procedures employ a flexible endoscope during the procedure. Flexible endoscopes often have a flexible, steerable articulating section near the distal end that can be controlled by the clinician by utilizing controls at the proximal end. Some flexible endoscopes are relatively small (1 mm to 3 mm in diameter), and may have no integral accessory channel (also called biopsy channels or working channels). Other flexible endoscopes, including gastroscopes and colonoscopes, have integral working channels having a diameter of about 2.0 to 3.7 mm for the purpose of introducing and removing medical devices and other accessory devices to perform diagnosis or therapy within the patient. For example, end effectors for creating an energy-induced weld or seal. Certain specialized endoscopes or steerable overtubes are available, such as large working channel endoscopes having a working channel of 5 mm, or larger, in diameter, which can be used to pass relatively large accessories, or to provide capability to suction large blood clots. Other specialized endoscopes include those having two or more working channels.

A common task both in minimally invasive and open surgical environments is to grasp, cut and fasten tissue while leaving the cut ends hemostatic (e.g., not bleeding). For example, it is often desirable to cut and seal bodily lumens, such as individual blood vessels or tissue including various vasculature. When sealing a fluid-carrying bodily lumen, it is often necessary for the seal to have sufficient strength to prevent leakage of the fluid, which may exert considerable fluid pressure.

Instruments exist for simultaneously making a longitudinal incision in tissue and fastening the tissue on opposing sides of the incision. Such instruments commonly include an end effector having a pair of cooperating jaw members that, if the instrument is intended for minimally invasive applications, are capable of passing through a cannula passageway or endoscopic working channel. In use, the clinician is able to close the jaw members to clamp the tissue to be cut. A reciprocating cutting instrument (or knife) is drawn distally along the jaw members to transect the clamped tissue. Simultaneously, a fastening mechanism fastens the cut ends of the tissue on opposing sides of the incision. Known fastening mechanisms include staples, sutures or various instruments utilizing energy sources. For example, various energy sources such as radiofrequency (RF) sources, ultrasound sources and lasers have been developed to coagulate, seal or join together tissue volumes.

SUMMARY

Various embodiments are directed to a surgical instrument comprising a handle, a shaft, an end effector, a reciprocating member and a cable. The shaft may be coupled to the handle and may extend distally along a longitudinal axis. The end effector may be positioned at a distal portion of the shaft and may comprise first and second jaw members. The first jaw member may define a first longitudinal slot and may comprise a first pulley positioned at a distal portion of the first jaw member. The second jaw member may define a second longitudinal slot and may be pivotable towards the first jaw member. The reciprocating member may be translatable distally and proximally parallel to the longitudinal axis, and may comprise a transverse member positioned to pass through the first and second longitudinal slots as the reciprocating member translates distally and proximally, at least one flange positioned on a distal portion of the reciprocating member to exert a force tending to close the first and second jaw members when the transverse member passes through the first and second longitudinal slots, and a distal leading edge that defines a blade. The cable may extend distally from the handle through the shaft to the first pulley and proximally from the first pulley to the reciprocating member, such that proximally directed motion of the cable exerts a distally directed force on the reciprocating member.

Also, various embodiments may be directed to a surgical instrument comprising a handle, a shaft, an end effector, a reciprocating member and a handle. The shaft may be coupled to the handle and may extend distally along a longitudinal axis. The end effector may be positioned at a distal portion of the shaft, and may comprise a stationary first jaw member and a pivotable second jaw member. The first jaw member may define a first longitudinal slot and may comprise a first pulley positioned at a distal portion of the first jaw member; and a first electrode comprising a first electrically conductive portion and a positive temperature coefficient (PTC) portion. The second jaw member may define a second longitudinal slot, comprise a second electrode and be pivotable towards the first jaw member. The reciprocating member may be translatable distally and proximally parallel to the longitudinal axis, and may comprise a transverse member positioned to pass through the first and second longitudinal slots as the reciprocating member translates distally and proximally; at least one flange positioned on a distal portion of the reciprocating member to exert a force tending to close the first and second jaw members when the transverse member passes through the first and second longitudinal slots; and a distal leading edge that defines a blade. The cable may extend distally from the handle through the shaft to the first pulley and proximally from the first pulley to the reciprocating member, such that proximally directed motion of the cable exerts a distally directed force on the reciprocating member.

Additionally, various embodiments may be directed to a surgical instrument comprising a handle, a shaft, an end effector, a reciprocating member and a cable. The shaft may be coupled to the handle and may extend distally along a longitudinal axis. The end effector may be positioned at a distal portion of the shaft and may comprise first and second jaw members and a collar. The first jaw member may comprise a first pulley positioned at a distal portion of the first jaw member. The second jaw member may be pivotable towards the first jaw member. The reciprocating member may be translatable distally and proximally parallel to the longitudinal axis and may comprise a transverse member and a distal leading edge. The transverse member may be positioned to pass through the first and second longitudinal slots as the reciprocating member translates distally and proximally. The distal leading edge may define a blade. The collar may be translatable distally and proximally from a position proximal from a pivot point of the second jaw member to a position distal from the pivot point of the second jaw member. The cable may extend distally from the handle through the shaft to the first pulley and proximally from the first pulley to the collar, such that proximally directed motion of the cable exerts a distally directed force on the collar.

FIGURES

Various features of the embodiments described herein are set forth with particularity in the appended claims. The various embodiments, however, both as to organization and methods of operation may be understood in accordance with the following description taken in conjunction with the accompanying drawings as follows.

Figure 25:
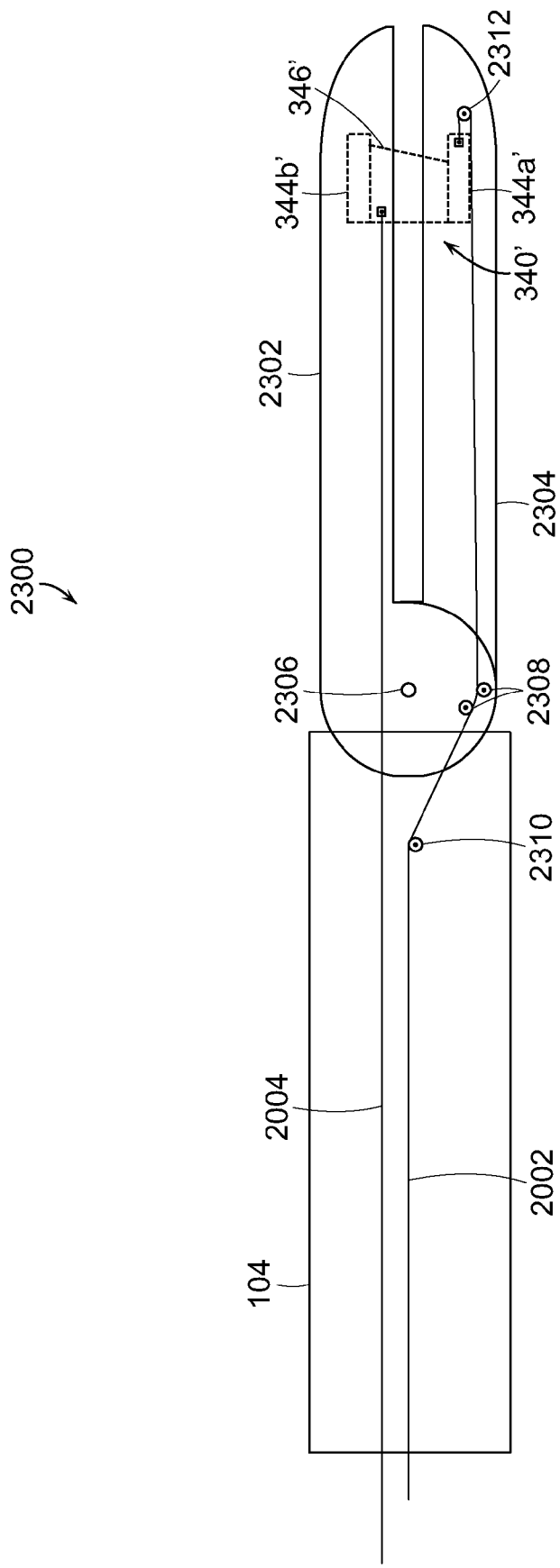
Figure 25A:
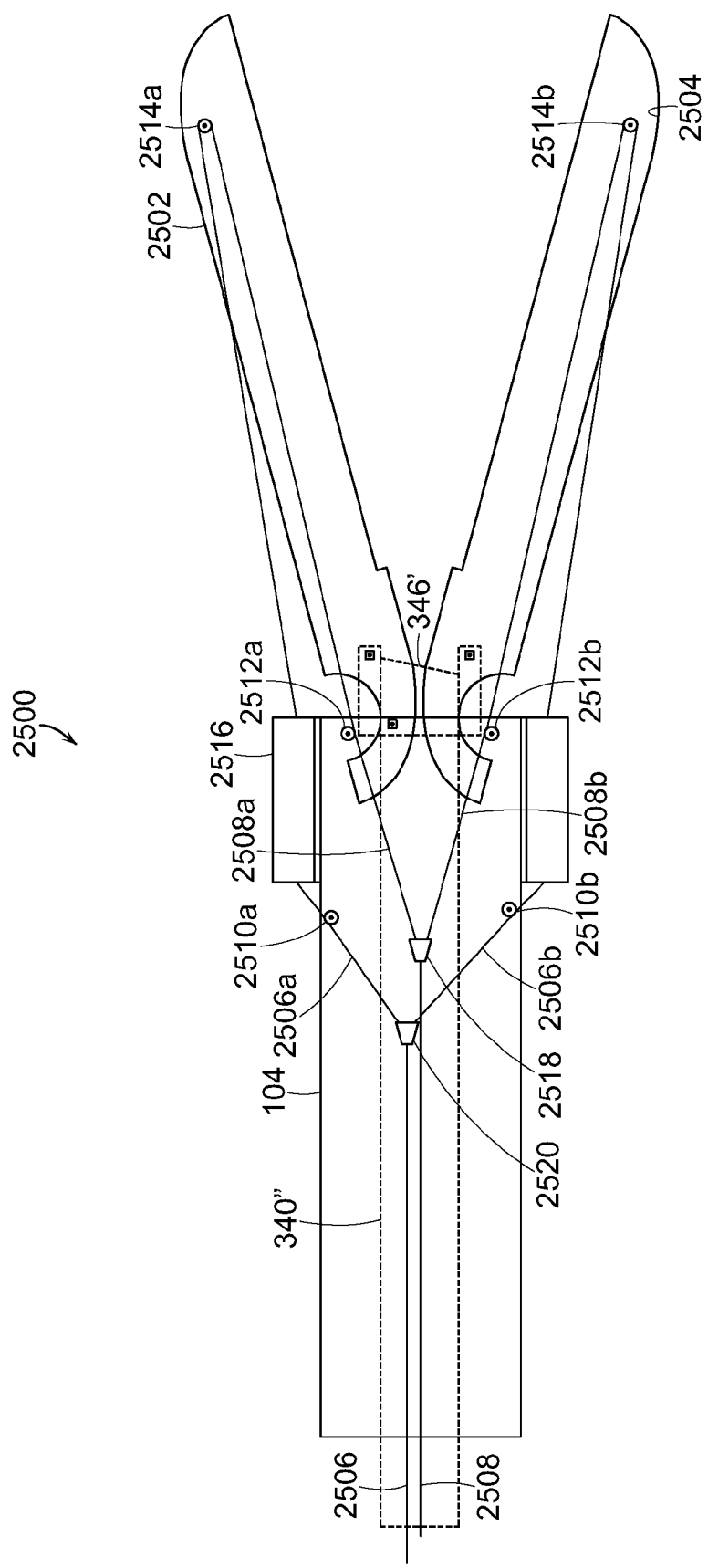
Figure 25B:
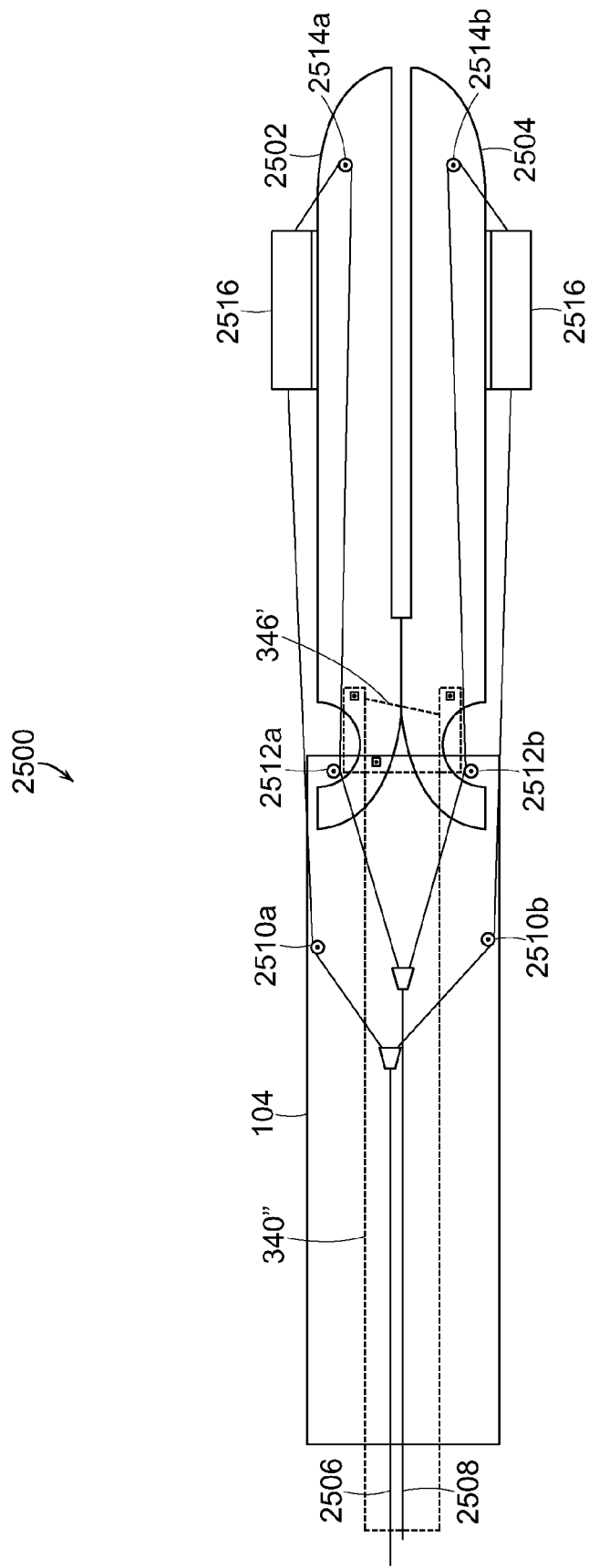

FIGS. 25*a*-25*b* illustrate one embodiment of an end effector 2500 with separately actuatable closure and cutting.

Figure 23:
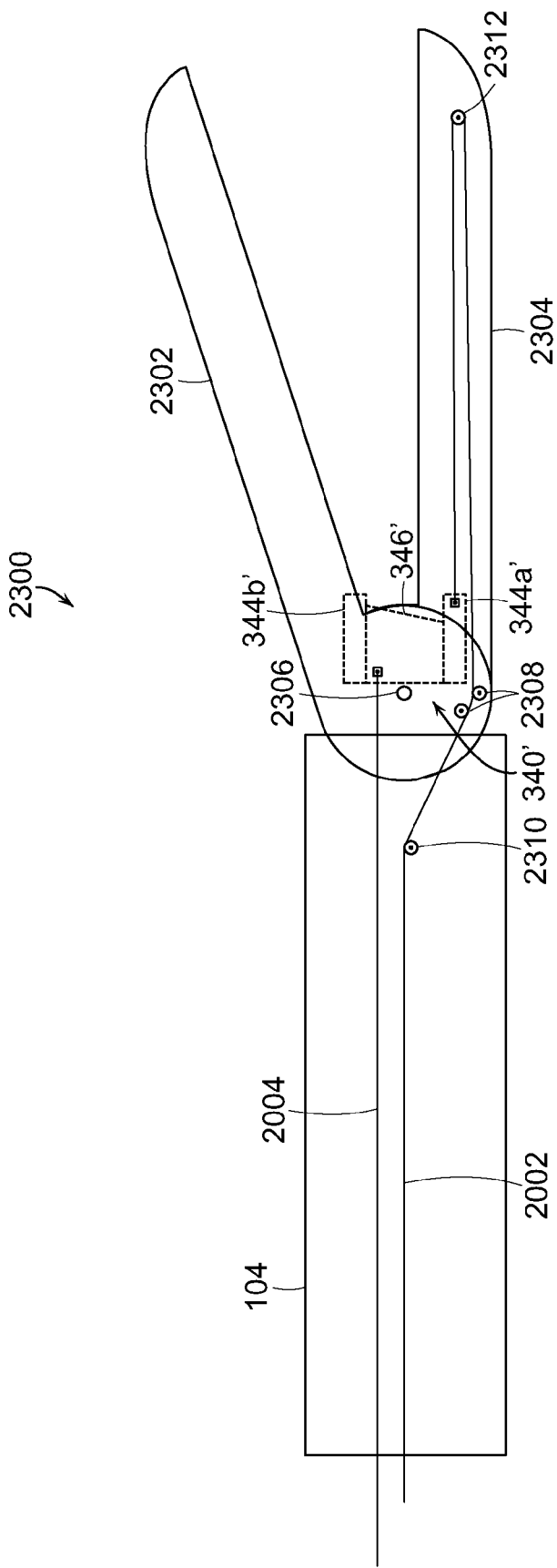
FIGS. 23-25 illustrate one embodiment of an end effector of the instrument shown in FIG. 3 having a cable-operated moving jaw member and a stationary jaw member.
Figure 24:
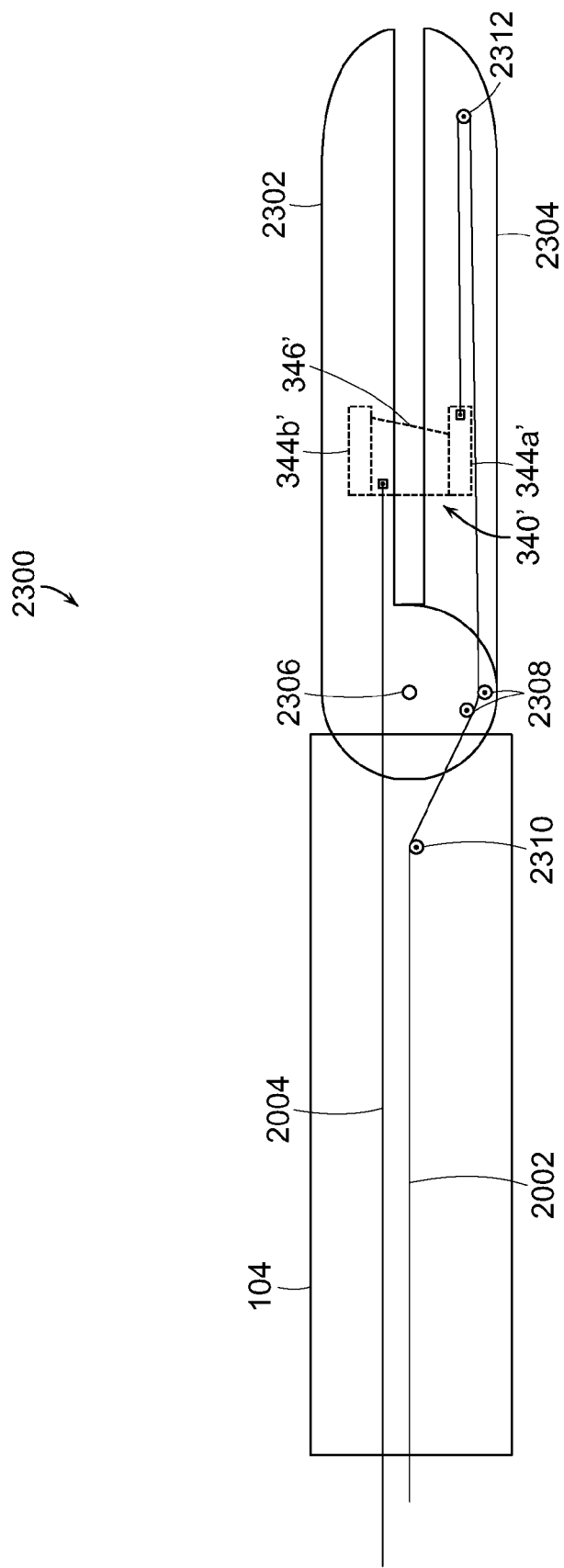
Figure 26:
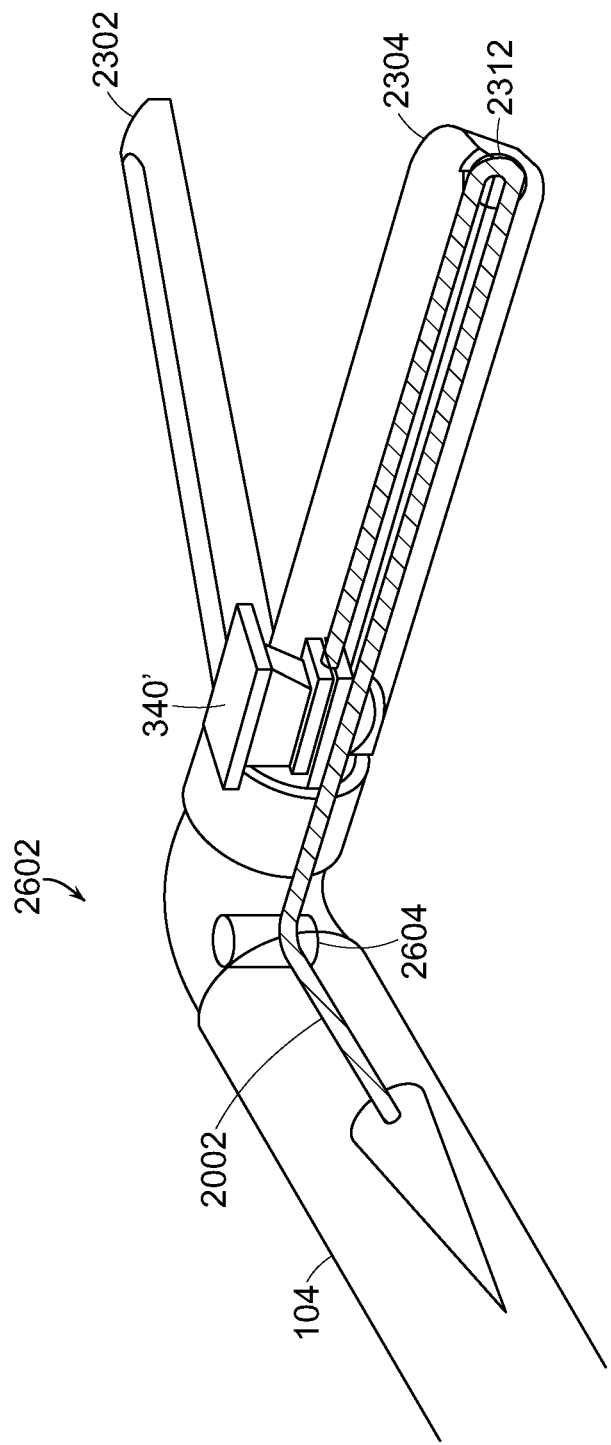

FIG. 26 illustrates one embodiment of the end effector of FIGS. 23-25 installed on a shaft comprising an articulation pivot.

Figure 27:
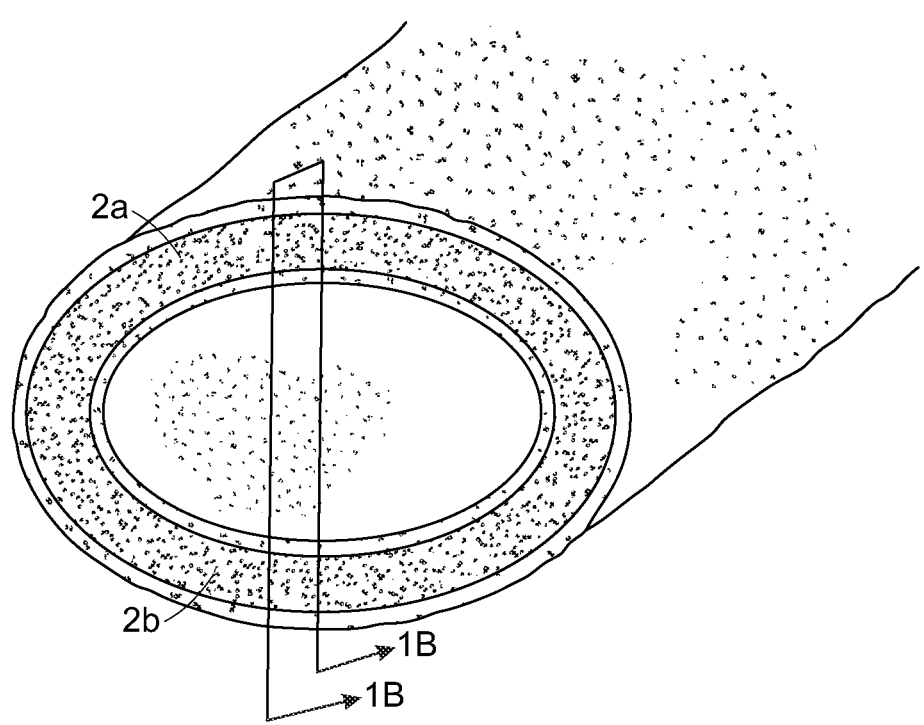

FIG. 27 shows an example embodiment of a vessel having opposing wall portions.

Figure 28:
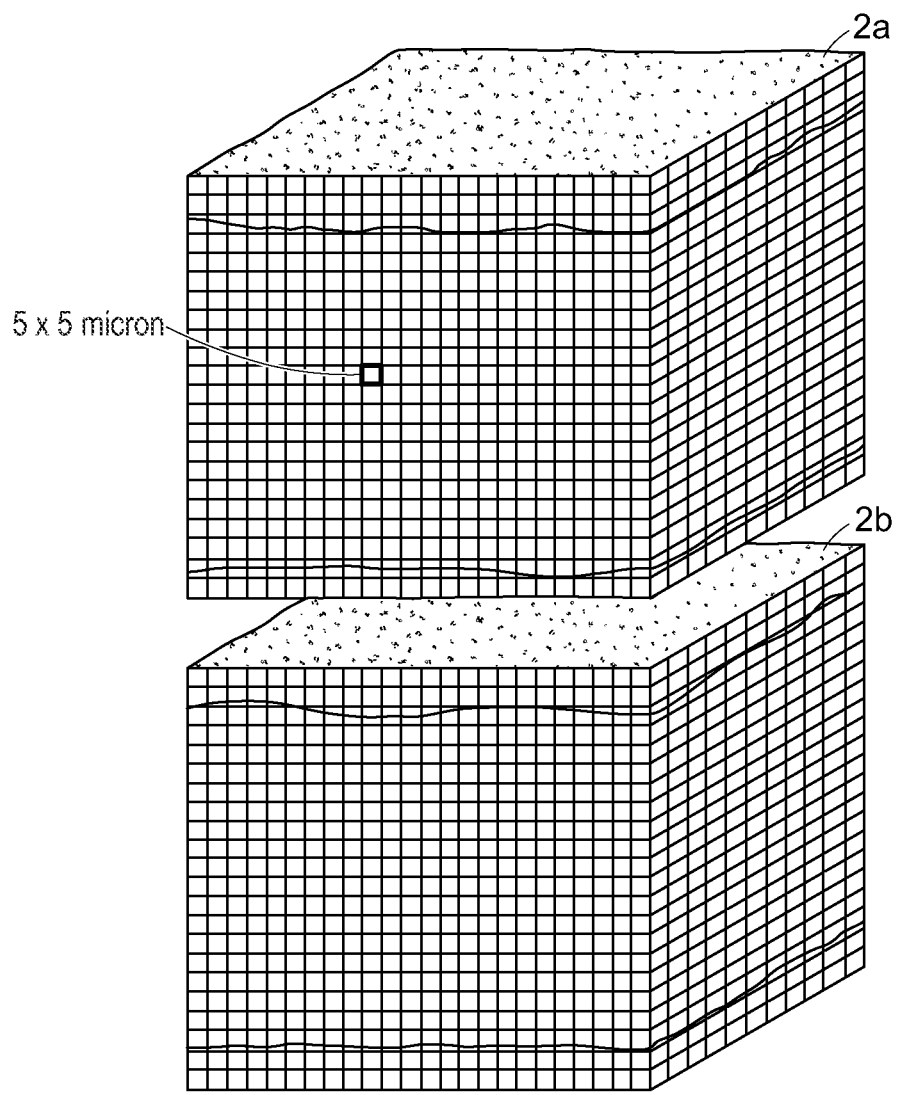

FIG. 28 is a graphic illustration of one embodiment of the opposing vessel walls portions of FIG. 27 with the tissue divided into a grid with arbitrary micron dimensions.

Figure 29:
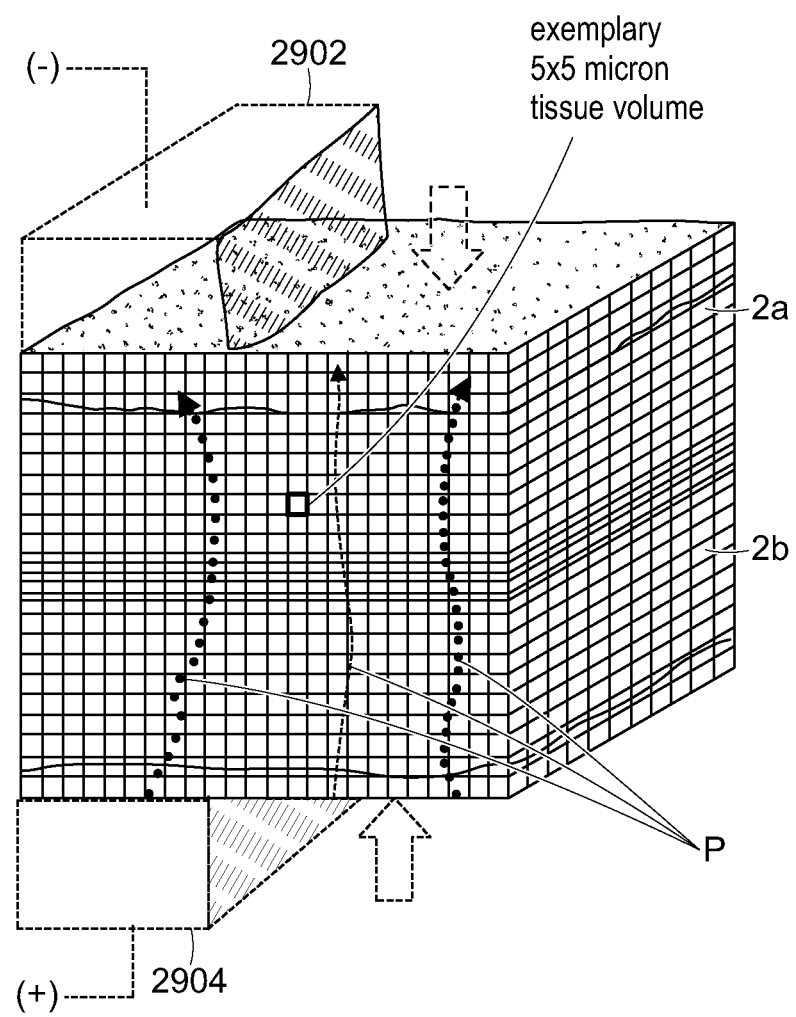

FIG. 29 illustrates one embodiment of the blood vessel of FIG. 27 acted upon by a device implementing a power adjustment approach to energy delivery.

Figure 30:
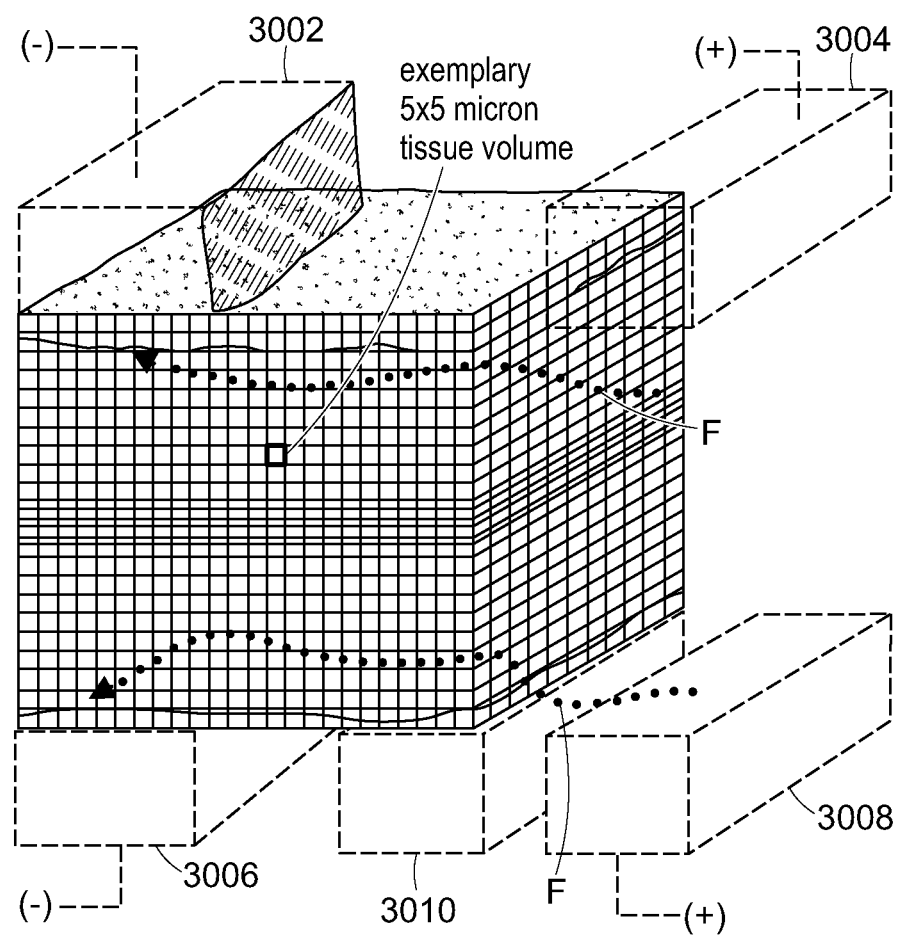

FIG. 30 illustrates one embodiment of the blood vessel of FIG. 27 acted upon by a device implementing a current-path directing approach to energy delivery.

Figure 31:
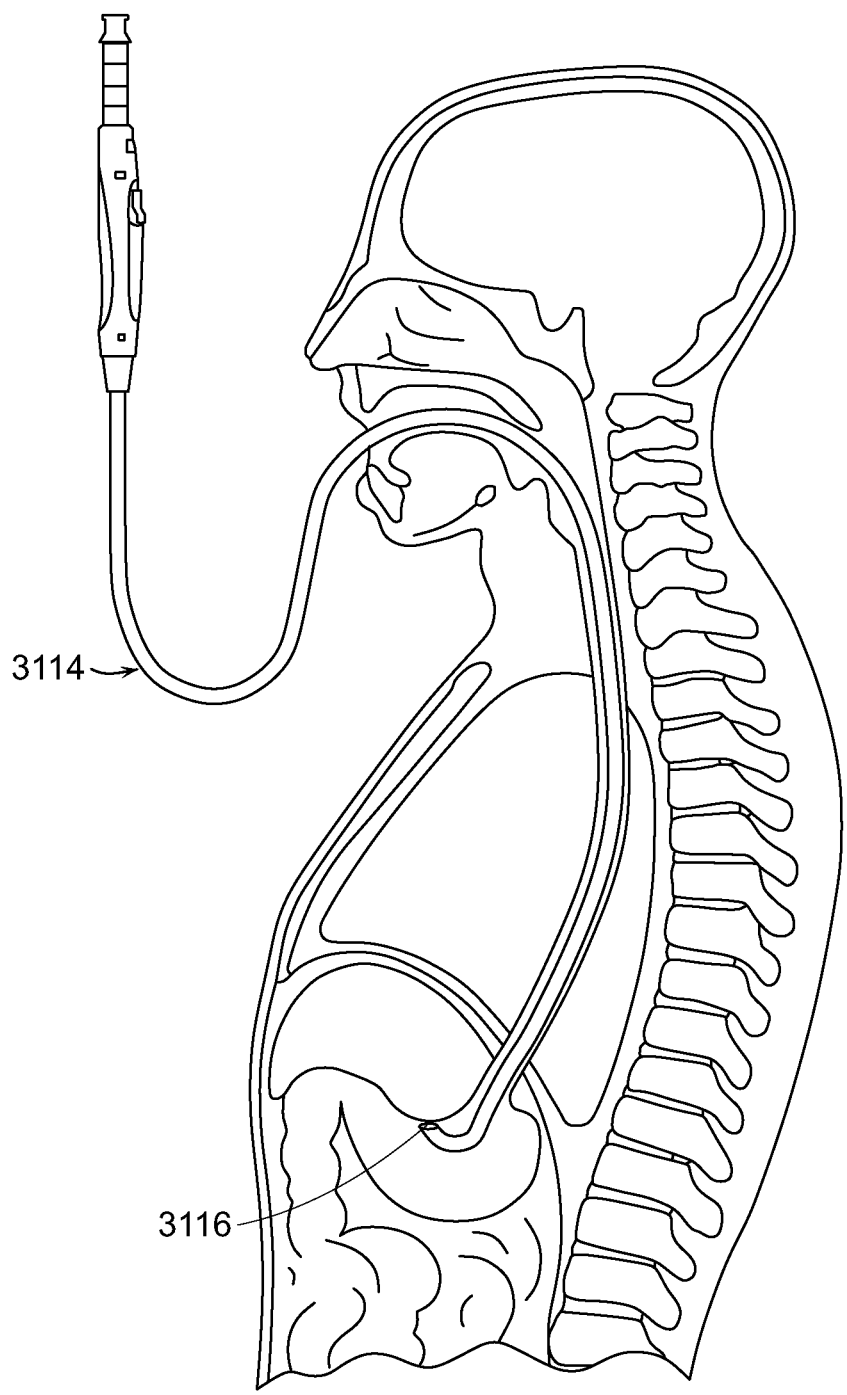

FIG. 31 illustrates one embodiment of an endoscope (illustrated here as a gastroscope) inserted into the upper gastrointestinal tract of a patient.

Figure 32:
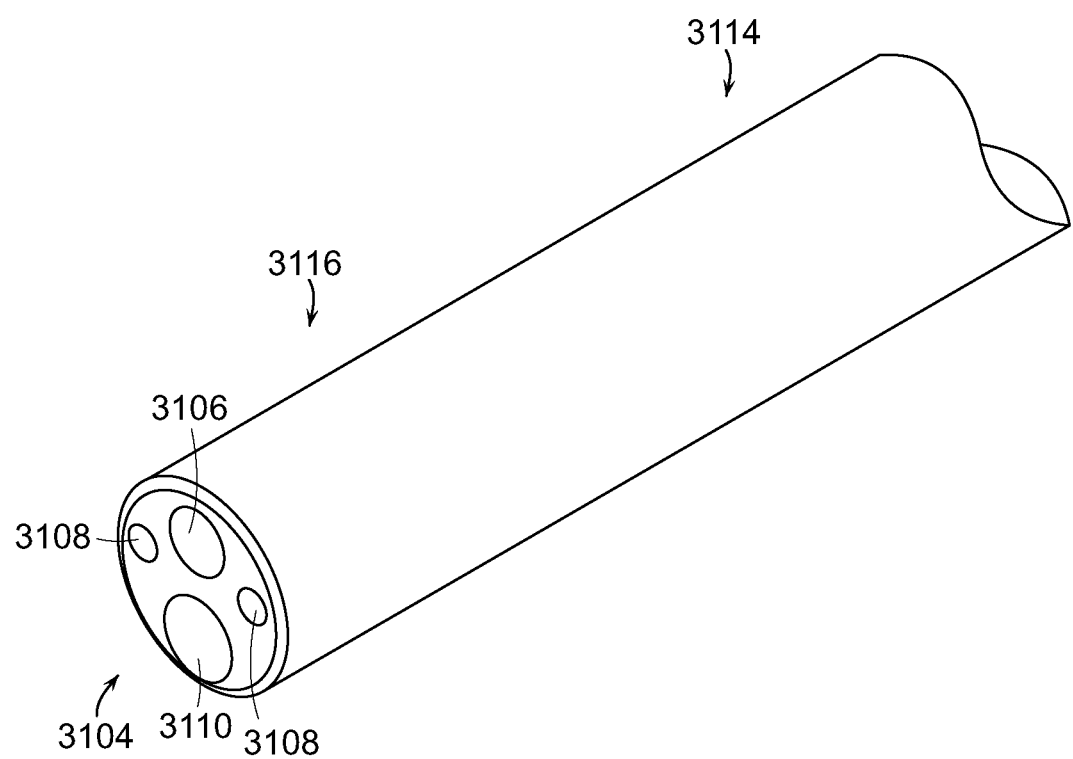

FIG. 32 illustrates one embodiment of a distal portion of the endoscope of FIG. 31, which may be used with the transection and sealing instrument described herein.

DESCRIPTION

Various embodiments are directed to cable actuated end effectors and surgical instruments comprising cable actuated end effectors. According to various embodiments, an end effector may comprise a pair of jaw members. One or both of the jaw members may be pivotable relative to one another such that the jaw members may transition from an open position to a closed position (or vice versa). A first cable may be routed from a handle of the surgical instrument through a shaft of the surgical instrumet to a pulley position within at least one of the jaw members. From the pulley, the cable may be routed proximally to a reciprocating member. A second cable may be routed from the reciprocating member to the handle via a shaft. To close the jaw members, a proximally directed force may be applied to the first cable. This may, in turn, cause the reciprocating member to be translated distally through slots in the jaw members. Flanges of the reciprocating member may ride above the slots tending to close the jaw members with a compressive force. To open the jaw members, a proximally directed force may be applied to the second cable, which may pull the reciprocating member proximally, allowing the jaw members to open.

Figure 1:
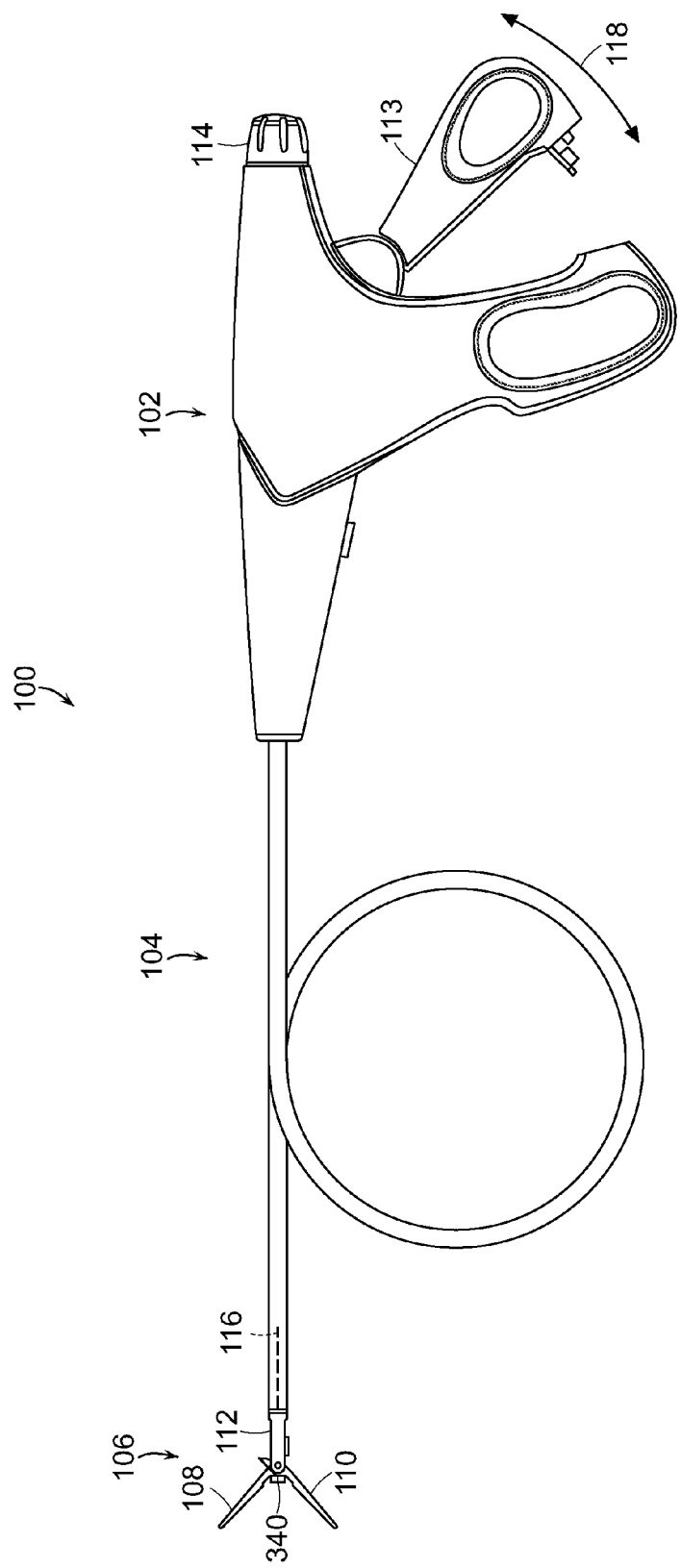
FIG. 1 illustrates one embodiment of a transection and sealing instrument, which may be used, for example, with an endoscope.

FIG. 1 illustrates one embodiment of a transection and sealing instrument 100. The instrument 100 may be used with an endoscope, laparoscope, or any other suitable introduction device. According to various embodiments, the transection and sealing instrument 100 may comprise a handle assembly 102, a shaft 104 and an end effector 106. The shaft 104 may be rigid (e.g., for laparoscopic application and/or open surgical application) or flexible, as shown, (e.g., for endoscopic application). In various embodiments, the shaft 104 may comprise one or more articulation points. The end effector 106 may comprise a first jaw member 108 and a second jaw member 110. The first jaw member 108 and second jaw member 110 may be connected to a clevis 112, which, in turn, may be coupled to the shaft 104. In various embodiments, as illustrated below, the jaw members 108, 110 may be directly coupled to the shaft 104 and the clevis 112 may be omitted. As illustrated in FIG. 1, the end effector 106 is shown with the jaw members 108, 110 in an open position. A reciprocating member 340 is illustrated between the jaw members 108, 110.

Figure 2:
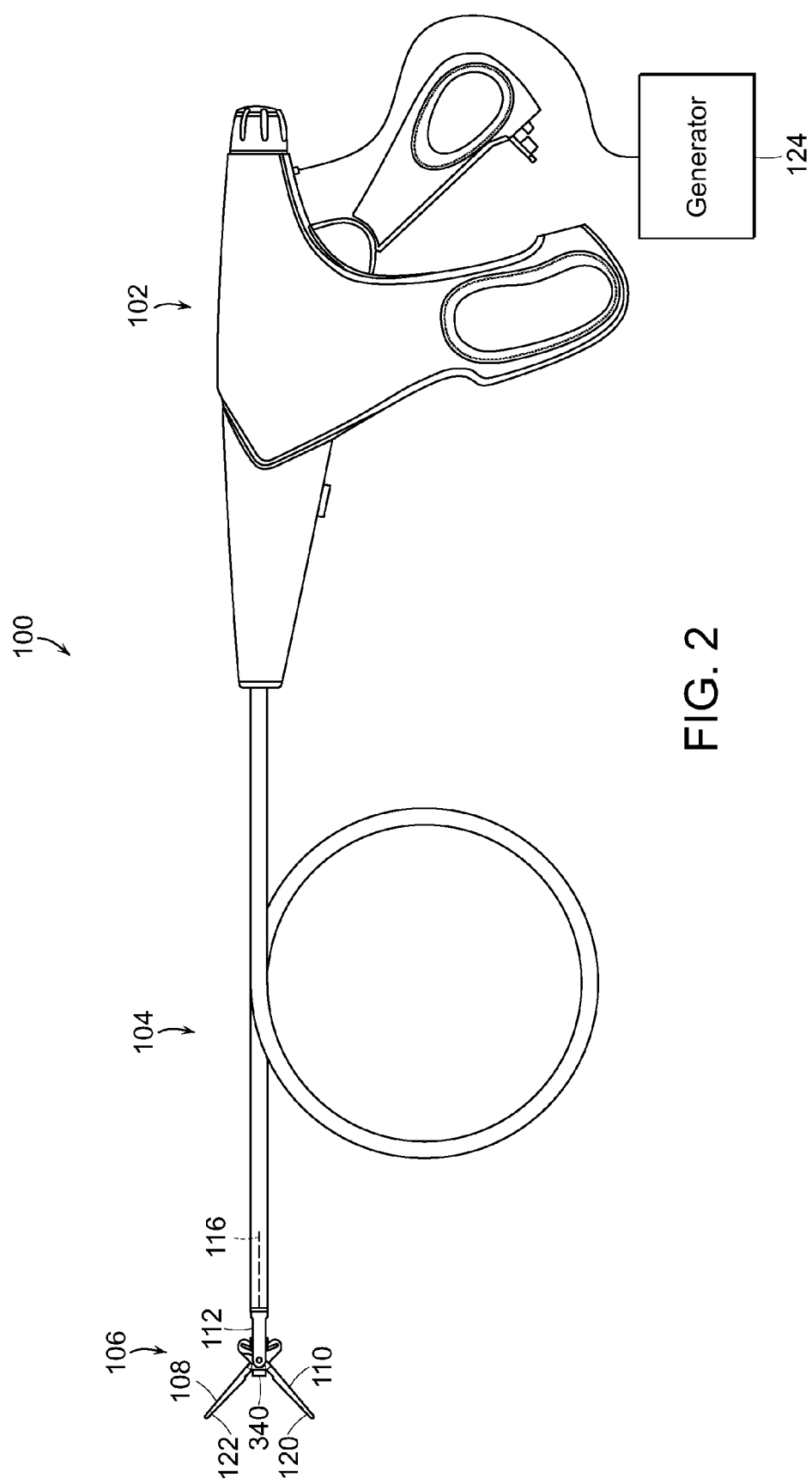
FIG. 2 illustrates one embodiment of the transection and sealing instrument of FIG. 1 for use in electrosurgical applications.

According to various embodiments, one or both of the jaw members 108, 110 may include, or serve as electrodes in monopolar or bi-polar electrosurgical applications including, for example, cutting, coagulation and welding. FIG. 2 illustrates one embodiment of the transection and sealing instrument 100 for use in electrosurgical applications. The jaw members 108, 110 of the end effector 106 may comprise respective electrodes 120, 122. The electrodes 120, 122 may be connected to an electrosurgical generator 124 via wires (not shown) extending from the end effector 106 through the shaft 104 and handle 102. The generator 124 may generate any suitable type of signal for electrosurgical applications. For example, the generator 124 may make various alternating current (A/C) and/or direct current (D/C) signals at suitable voltages, currents, frequencies and wave patterns. According to various embodiments, the transection and sealing instrument 100 may be configured for monopolar operation. In this case, the end effector 106 may comprise a single electrode, rather than two. According to various embodiments, all or a portion of the end effector 106 may serve as the single electrode.

A translating member 116 may extend within the shaft 104 from the end effector 106 to the handle 102. The translating member 116 may be made from any suitable material. For example, the translating member 116 may be, a metal wire (e.g., a tri-layered steel cable), a plastic or metal shaft, etc. In some embodiments, one or more additional translating members (not shown in FIG. 2) may be included to control the motion of the end effector 106 and/or the shaft 104. In various embodiments, the instrument 100 may comprise multiple translating members 116, for example, as described below. At the handle 102, the shaft 104 may be directly or indirectly coupled to an actuator 113 (FIG. 1). In use, a clinician may cause the actuator 113 to pivot along arrow 118 from a first position to a second position. When the actuator moves from the first position to the second position, it may translate the translating member 116 distally or proximally. Distal or proximal motion of the translating member 116 may, in turn, cause the end effector 106 to transition from an open position to a closed position (or vice versa) and/or to perform various other surgical activities such as, for example, severing and/or joining or welding. According to various embodiments, the handle 102 may comprise multiple actuators 113. When multiple actuators 113 are present, each actuator 113 may be used by a clinician to cause the end effector 106 to perform different surgical activities. In various embodiments a single actuator 113 may cause the end effector 106 to perform more than one activity. For example, a clinician may activate a single actuator 113 to force a reciprocating member 340 distally. This may, as described, both close the jaw members 108, 110 and transect any tissue between the jaw members 108, 110.

Figure 3:
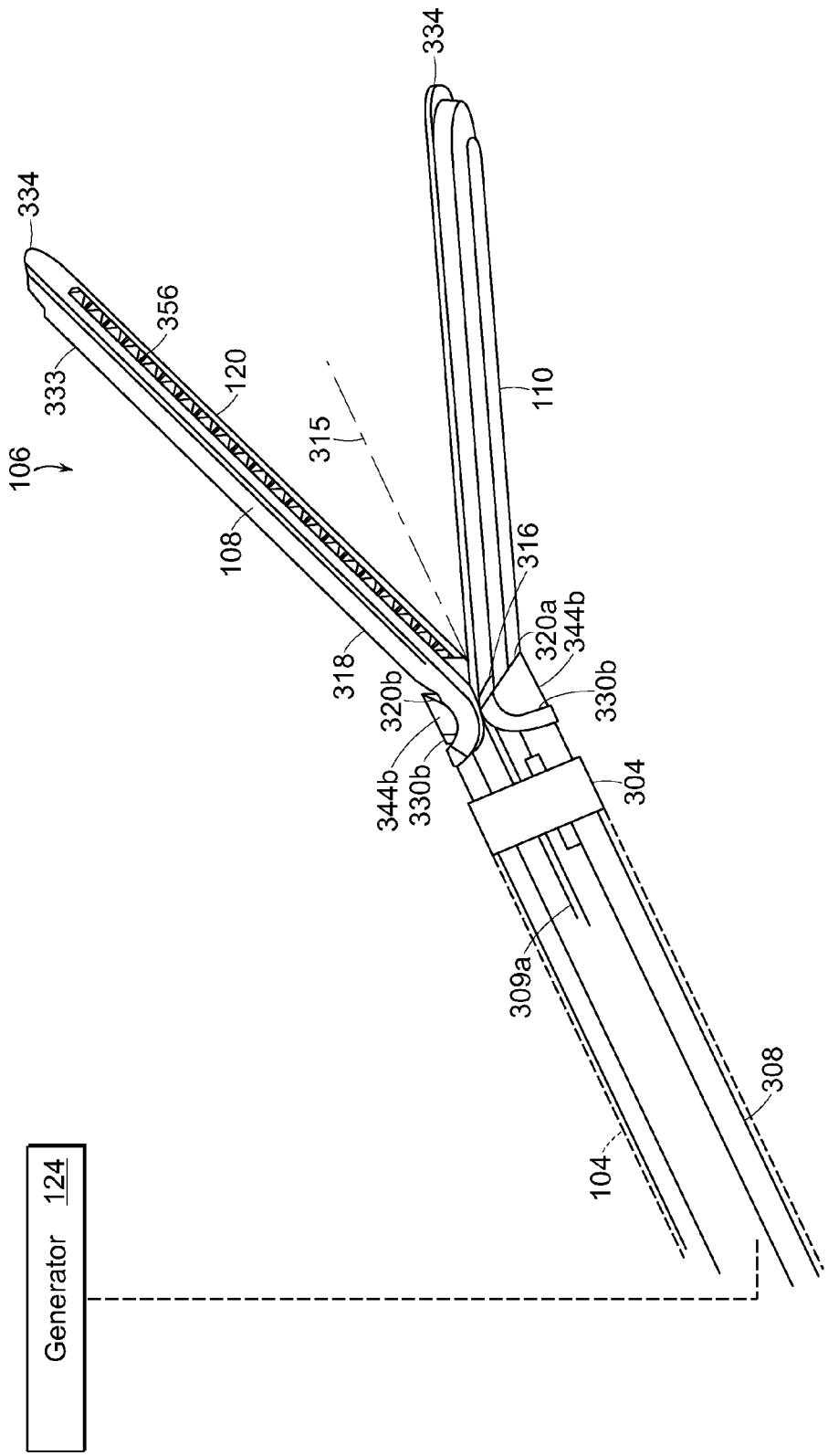
FIGS. 3 and 4 illustrate one embodiment of an end effector of a surgical grasping instrument adapted for transecting captured tissue and contemporaneous sealing of the captured tissue with RF energy delivery.
Figure 4:
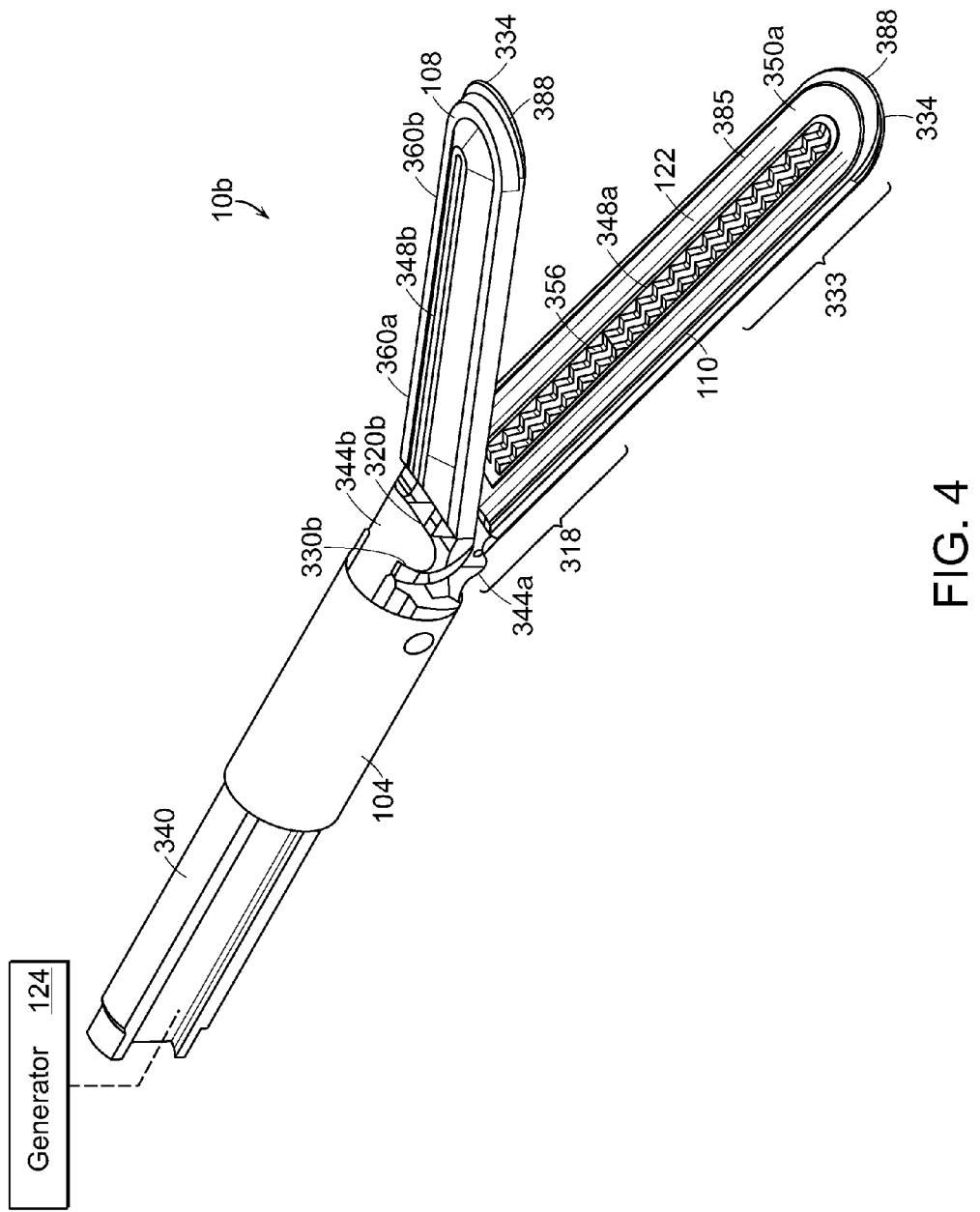

FIGS. 3 and 4 illustrate one embodiment of an end effector 106 of the instrument 100 adapted for transecting captured tissue and contemporaneous sealing of the captured tissue with RF energy delivery. The end effector 106 is carried at the distal end 304 of the shaft 104 that can be rigid, articulatable or deflectable in any suitable diameter. For example, the shaft 104 can have a diameter ranging from about 2 mm to 20 mm to cooperate with cannulae in endoscopic/laparoscopic surgeries or for use in open surgical procedures. The shaft 104 extends from a proximal handle, such as the handle 102. The handle 102 can be any type of pistol-grip or other type of handle known in the art that carries actuator levers, triggers or sliders for moving the translating member 116 or members distally and proximally to actuate the jaws as will be disclosed below. The shaft 104 has a bore 308 extending therethrough for carrying actuator mechanisms (e.g., translating member 116) for actuating the jaws and for carrying electrical leads 309a-309b for the electrosurgical components of the end effector 106.

FIGS. 3 and 4 show details of the end effector 106, including the (upper) jaw element 108 and (lower) jaw element 110 that are adapted to close or approximate along an axis 315. The jaw elements 108, 110 may both be moveable or a single jaw may rotate to provide the open and closed positions. In the exemplary embodiment of FIGS. 1 and 2, both the lower and upper jaws 110, 108 are moveable relative to a rolling pivot location 316 defined further below.

An opening-closing mechanism of the end effector 106 operates on the basis of cam mechanisms that provide a positive engagement of camming surfaces both distal and proximal to a pivoting location (i) for moving the jaw assembly to the (second) closed position to engage tissue under very high compressive forces, and (ii) for moving the jaws toward the (first) open position to apply substantially high opening forces for "dissecting" tissue. This feature allows the surgeon to insert the tip of the closed jaws into a dissectable tissue plane—and thereafter open the jaws to apply such dissecting forces against the tissues.

Figure 5:
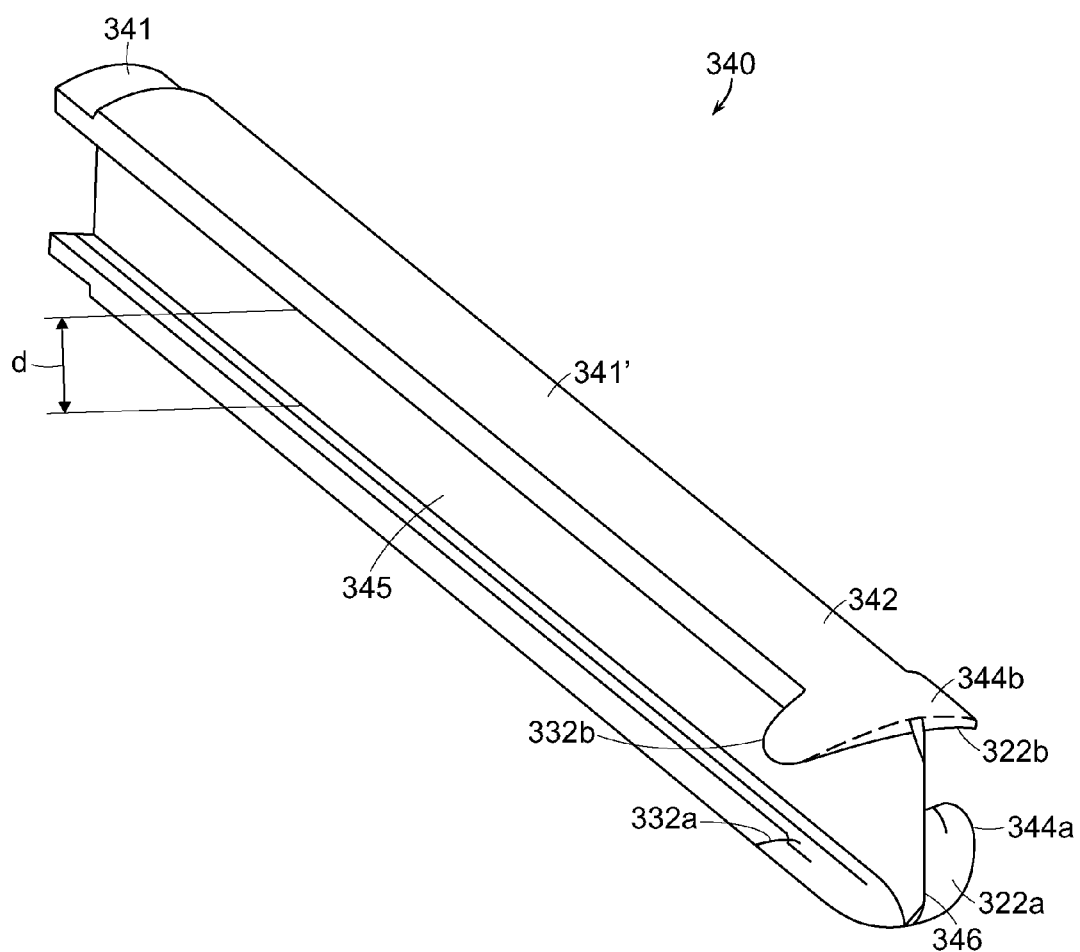
FIGS. 5 and 6 illustrate one embodiment of the reciprocating member shown in FIGS. 3 and 4.
Figure 6:
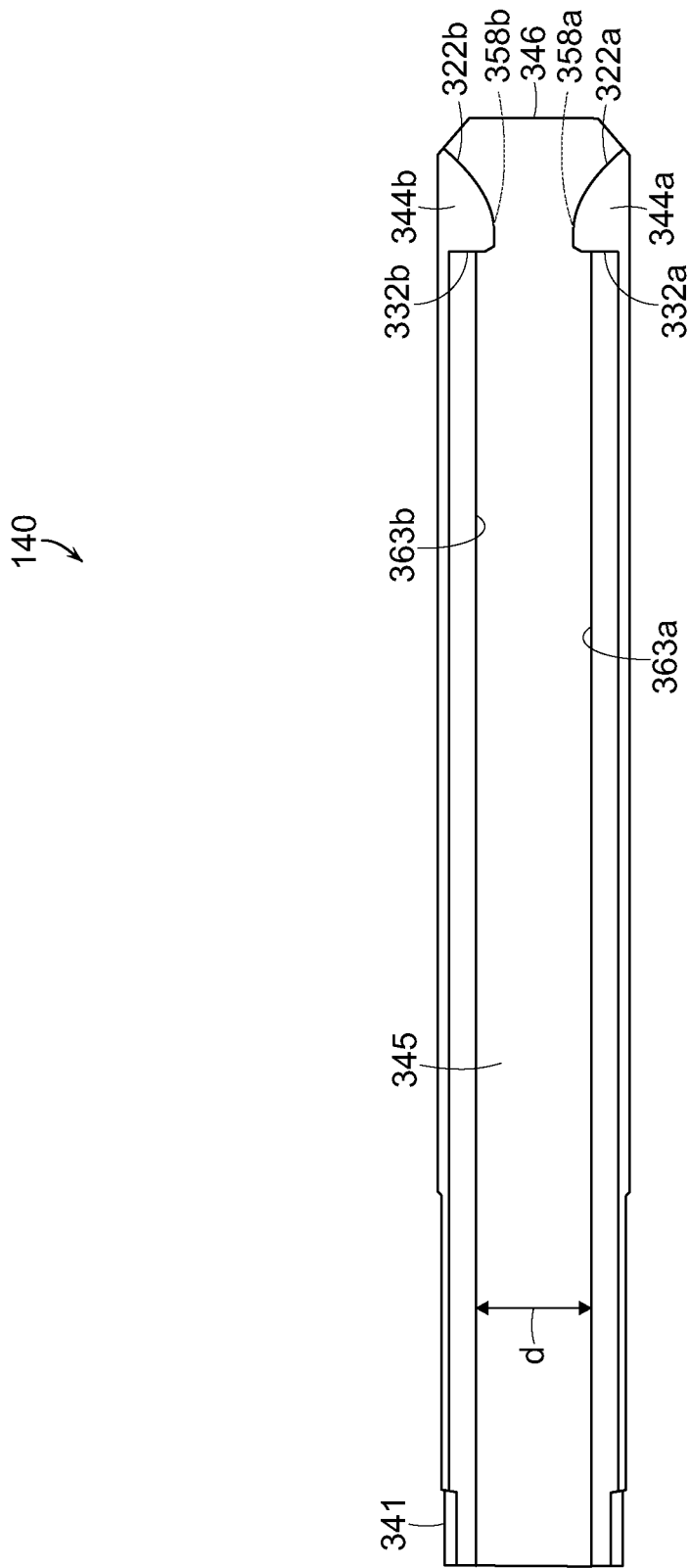

According to various embodiments, the lower and upper jaws 110, 108 may have a first end 318, in the open position, that defines first (proximally-facing) arcuate outer surface portions indicated at 320a and 320b that are engaged by a first surface portions 322a and 322b of a reciprocatable I-beam member 340 (FIG. 4) that is adapted to slide over the jaw elements 108, 110 to thereby move the jaws toward closed position. FIGS. 5 and 6 show views that illustrate the cam surfaces of reciprocating member 340 de-mated from jaws 110 and 108. The first end portion 318 of the lower and upper jaws, in the open position, further defines second (distally-facing) arcuate surface portions indicated at 330a and 330b that are engaged by second surface portions 332a and 332b (FIG. 5) of the reciprocatable member 340 for moving the jaw elements to the open position. The effective point of jaw rotation may lie between the first and second arcuate cam surfaces of the jaws. The distal (second) end region 333 of the paired jaws is rounded with a lip 334 that can serve as an electrode for surface coagulation as will be described below.

In this embodiment of FIGS. 3, 4 and 5, the reciprocating member 340 may be actuatable from the handle of the instrument by any suitable mechanism, such as actuator 113, which may be coupled to a proximal end 341 of member 340. The proximal end 341 and medial portion 341' of member 340 are dimensioned to reciprocate within bore 308 of the shaft 104. The distal portion 342 of reciprocating member 340 carries first (lower) and second (upper) laterally-extending flanges or shoulder elements 344A and 344B that are coupled by an intermediate transverse element 345. The transverse element 345 further is adapted to transect tissue captured between the jaws with a leading edge 346 (FIG. 5) that can be a blade or a cutting electrode. The transverse element 345 is adapted to slide within channels 348a and 348b in the paired first and second jaws 110, 108. As can be seen best in FIGS. 5 and 6, the laterally-extending shoulder elements 344A and 344B define the surfaces 322a, 322b, 332a, 332b that slidably engage the arcuate cam surfaces of the jaws and that apply high compressive forces to the jaws in the closed position.

According to various embodiments, the first and second jaws 108 and 110 may define tissue-engaging surfaces or planes 350a and 350b that contact and deliver energy to engaged tissues, in part, from RF electrodes 120, 122. The engagement plane 350a of the lower jaw 110 may be adapted to deliver energy to tissue, and the tissue-contacting surface 350B of upper jaw 108 may be electrosurgically active or passive as will be described below. Alternatively, the engagement surfaces 350a, 350b of the jaws can carry any suitable electrode arrangement known in the art.

The jaws 108, 110 may have teeth or serrations 356 in any location for gripping tissue. The embodiment of FIGS. 3 and 4 depicts such serrations 356 at an inner portion of the jaws along channels 348a and 348b thus leaving engagement planes 350a and 350b laterally outward of the tissue-gripping elements. The serrations 356 may be of any suitable symmetric or asymmetric shape or combination of shapes including, for example, triangular, rounded, sinusoidal, etc. In the embodiments described below, the engagement planes 350a and 350b and electrode(s) 120, 122 generally are shown with a non-serrated surface for clarity of explanation, but such engagement planes and electrodes themselves can be any non-smooth gripping surface. The axial length of jaws 108, 110 indicated at L can be any suitable length depending on the anatomic structure targeted for transection and sealing. In various embodiments, the length L may be between 10 mm and 50 mm. In some embodiments, the length L may be longer. For example, one embodiment of an end effector 106 for resecting and sealing organs such as a lung or liver may have a length L of about 200 mm. Also, for example, for some surgical tasks, the jaws having a shorter length L may be used, including, for example, jaws having a length L of about 5.0 mm.

Figure 9:
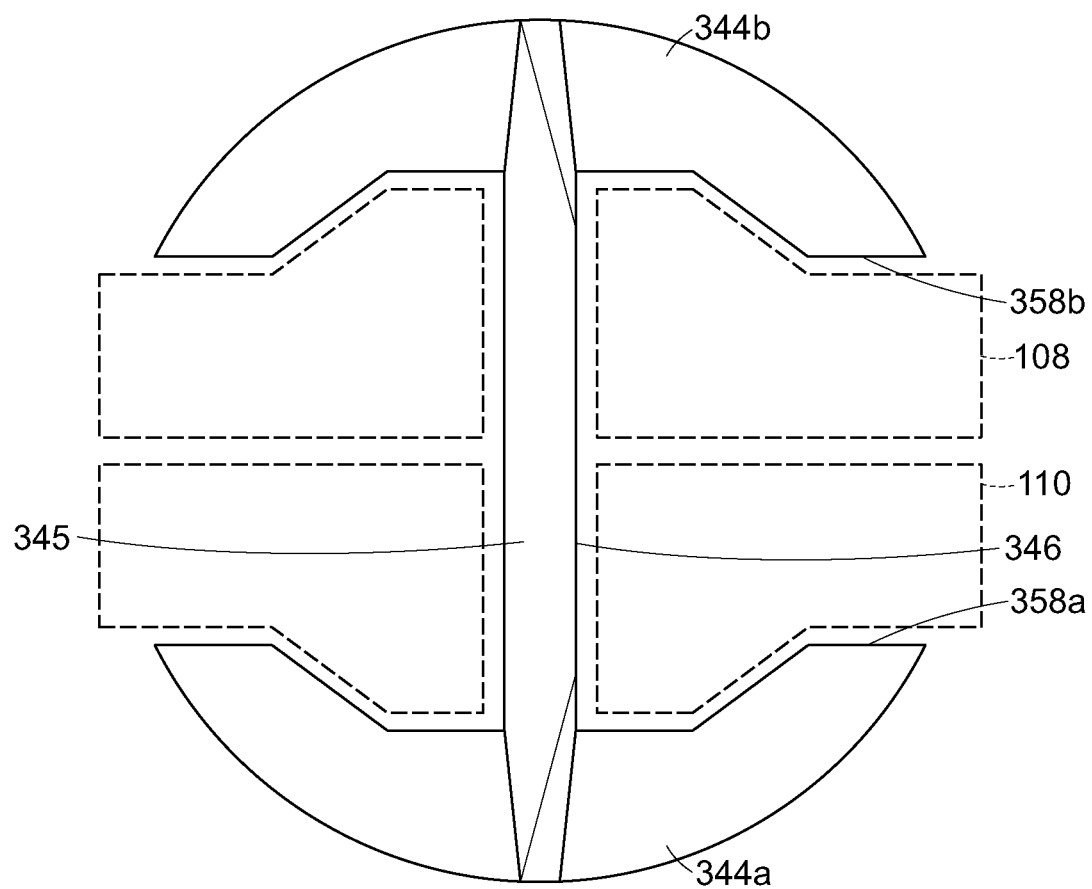
FIG. 9 illustrates an end view of one embodiment of the reciprocating member of FIG. 3 with the jaws of the end effector in phantom view.
Figure 10:
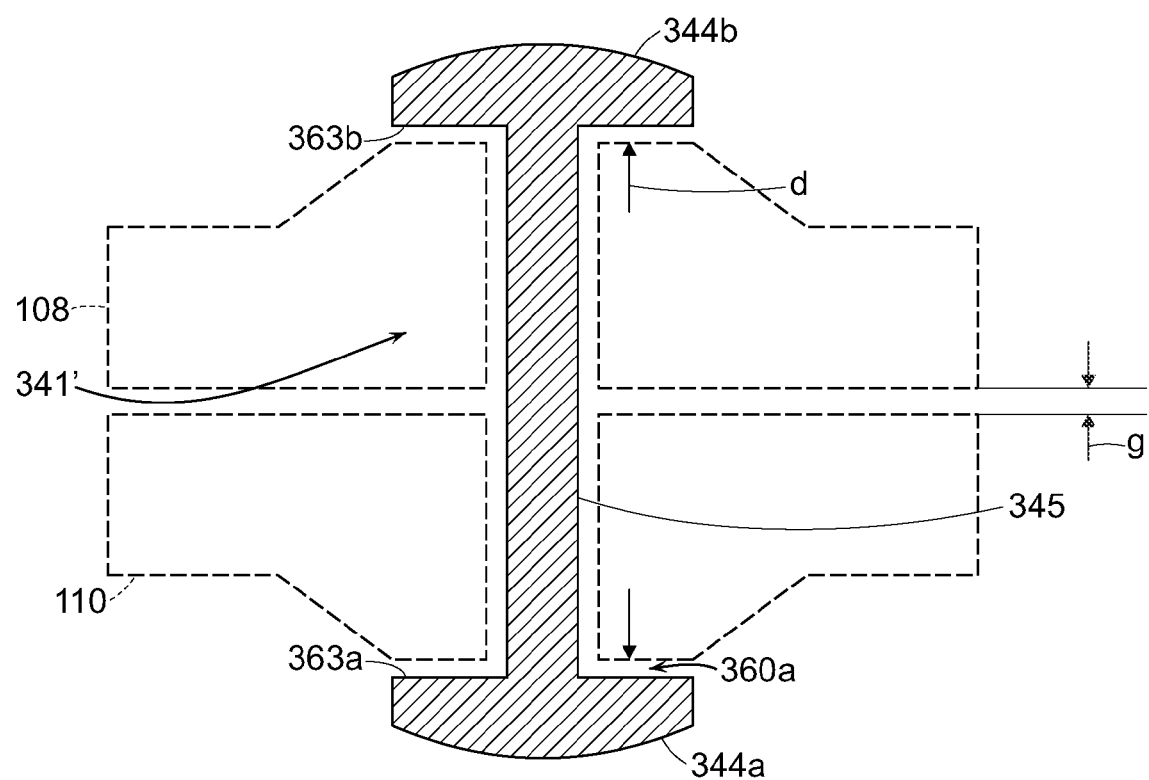
FIG. 10 illustrates a cross-sectional view of the embodiment shown in FIG. 9 along a cross-section taken at a position proximally located from the end view shown in FIG. 9.

FIG. 9 illustrates an end view of one embodiment of the reciprocating member 340 with the jaws 110 and 108 in phantom view. The view shown in FIG. 9 is a head-on view with the distally positioned blade surface 346 pointed out of the page. FIG. 10 illustrates a cross-sectional view of the embodiment shown in FIG. 9 along a cross-section taken at a position proximally located from the end view shown in FIG. 9. The transverse element 345 of the reciprocating member 340 may define a transverse dimension d between innermost surfaces 358a and 358b of the flanges 344A, 344B of the reciprocating member 340 and cooperating medial and distal outer surfaces 360A and 360B of the jaws. The selected transverse dimension d between the flanges or shoulders 344A and 344B thus further defines the engagement gap g between the engagement planes 350a and 350b of the jaws in the closed position. It has been found that very high compression of tissue combined with controlled RF energy delivery is optimal for welding the engaged tissue volume contemporaneous with transection of the tissue. According to various embodiments, the engagement gap g between the engagement planes 350a, 350b may range from about 0.001" to about 0.050". For example, the gap g between the engagement planes ranges from about 0.001" to about 0.010". As can be seen in FIGS. 5 and 10, the medial portion 341' of the reciprocating member 340 may have an "I"-beam shape with inner surface portions 363a and 363b that engage the cooperating medial outer surfaces of the jaws. Thus, in various embodiments, the entire length L of the jaws can be maintained in a fixed spaced-apart relationship to define a consistent engagement gap g. According to various embodiments, the engagement gap g may be selected to be large enough to prevent tissue engaged between the jaws 108, 110 from being sheared and to prevent electrical shorts between the electrodes 120, 122.

Figure 7:
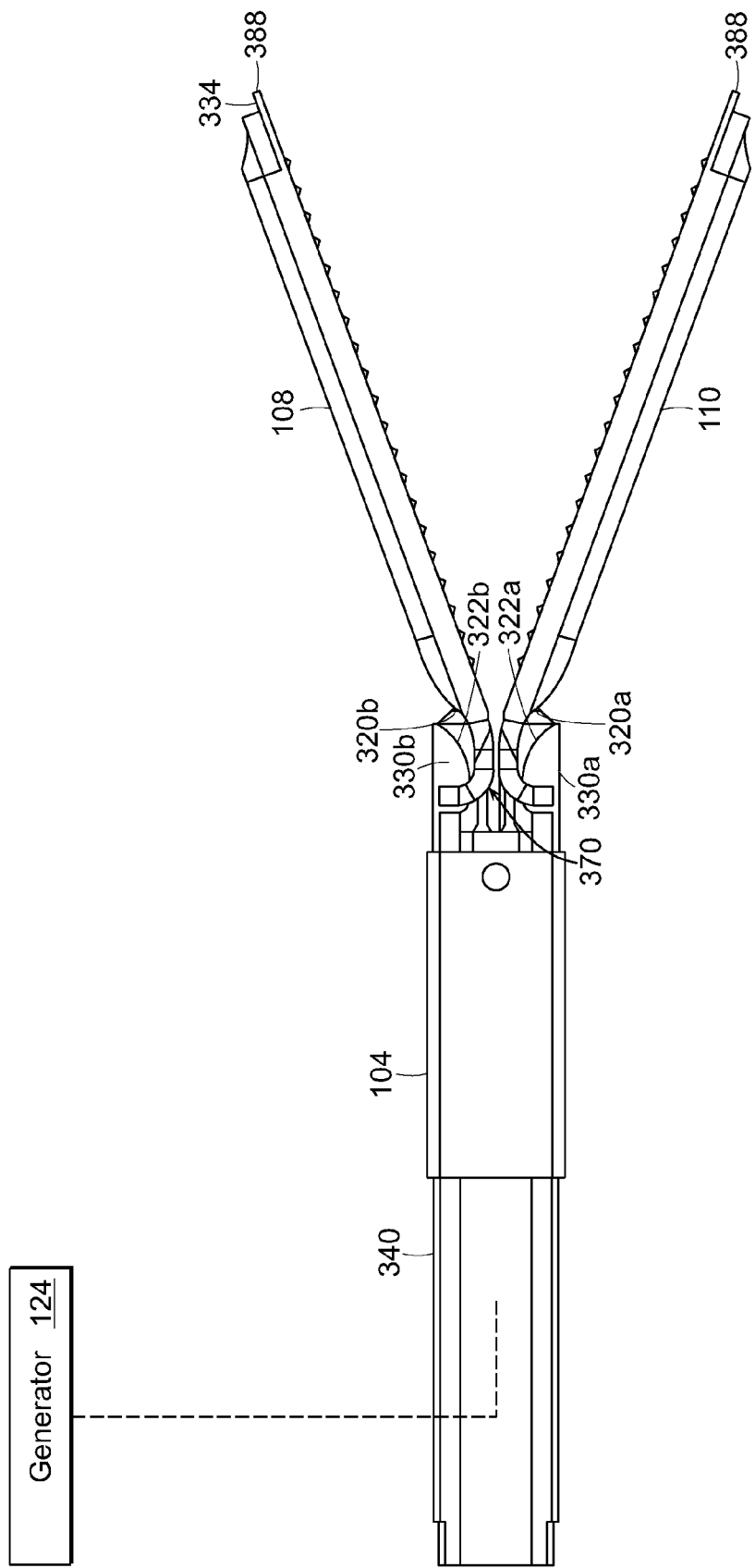
FIGS. 7 and 8 illustrate one embodiment of the actuation of a reciprocating member shown in FIG. 3 from a first retracted position to a second extended position to move the jaws of the end effector from an open position to a closed position.
Figure 8:
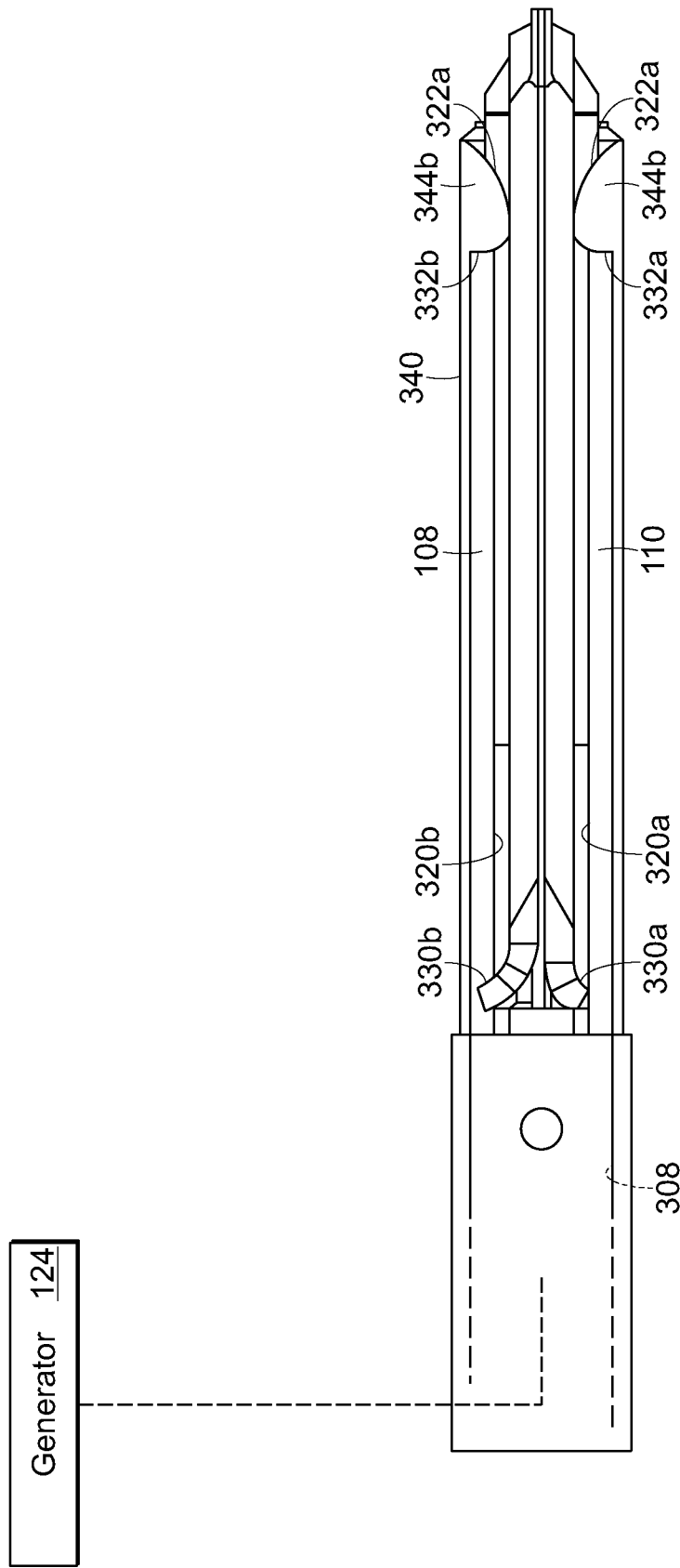

FIGS. 7 and 8 illustrate one embodiment of the actuation of the reciprocating member 340 from a first retracted position to a second extended position to move the jaws 110 and 108 from an open position to a closed position. Referring to FIG. 7, it can be seen that the translatable member 340 is being moved in the proximal direction so that the proximal-facing surfaces 332a and 332b (FIG. 5) of reciprocating member 340 about the outer surfaces 330a and 330b of the jaws thus forcing the jaws apart, for example to apply dissecting forces to tissues or to open jaws 108 and 110 to engage targeted tissues for hemostasis and transection. FIG. 8 shows the reciprocating member 340 after having been fully extended in the distal direction so that the distal-facing surfaces 322a and 322b of reciprocating member 340 have ridden up and over the proximal arcuate surfaces 320a and 320b of the jaws (and medial outer surfaces 360A and 360B) thus forcing the jaws together thereby producing a compressive force between jaws 108 and 110. According to various embodiments, the orientation of surfaces 322a, 322b of the reciprocating member 340 and/or the arcuate surfaces 320a, 320b may be modified to modify the compression rate provided by the reciprocating member 340. For example, the orientation of the 322a, 322b of the reciprocating member 340 and/or the arcuate surfaces 320a, 320b may vary from one embodiment to another, or may vary within a single embodiment in order to cause variable compression rates within a single stroke of the reciprocating member 340.

Figure 11:
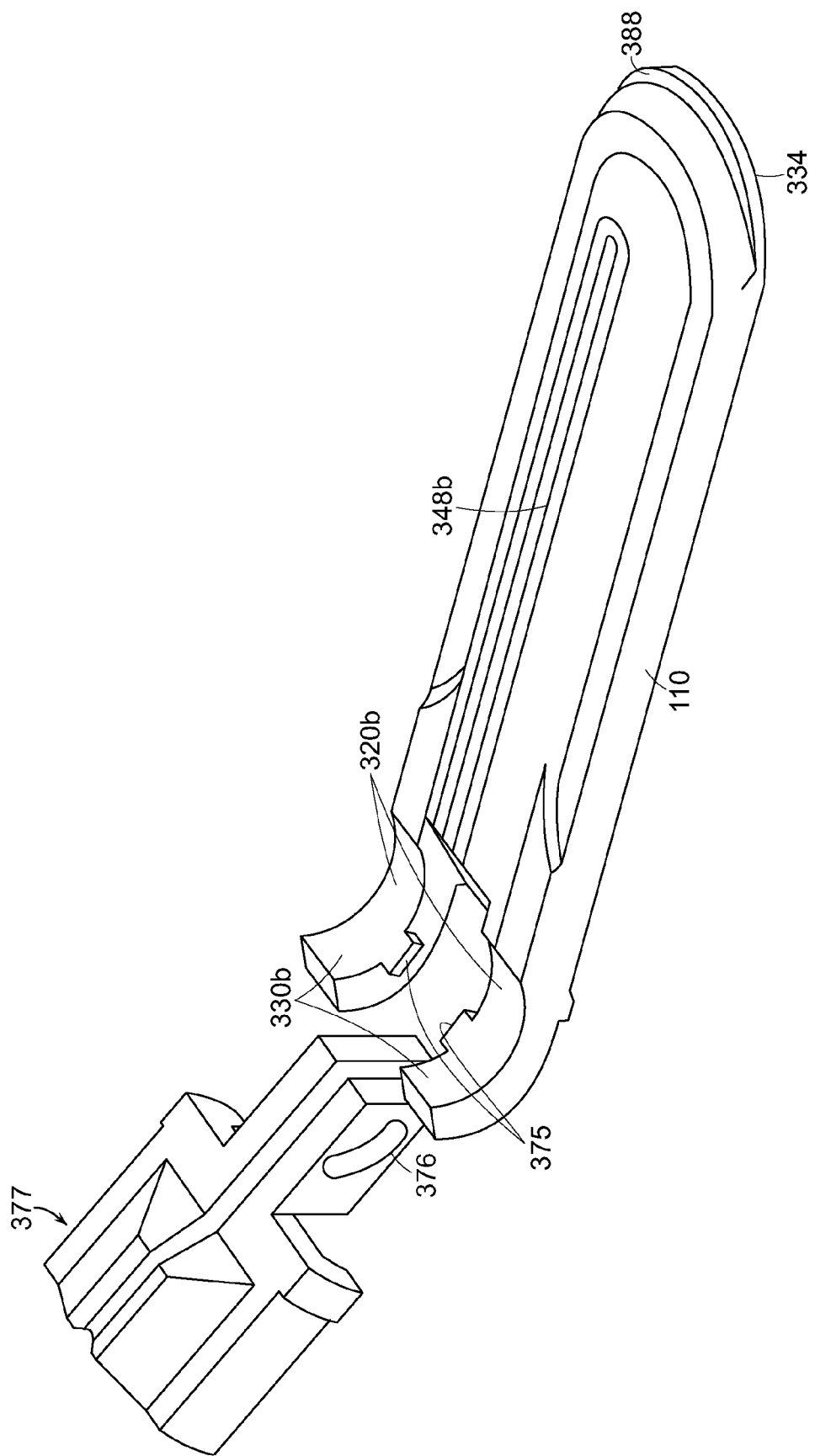
FIG. 11 illustrates one embodiment of the jaw of the end effector of FIG. 3 de-mated from the end effector.

According to various embodiments, the jaws 108, 110 may rollably contact one another along the interface 370 between inner surfaces 372 of the first end 318 of the jaws. As jaws 108 and 110 articulate, the pivot point is moving as the point of contact changes at the interface between surfaces 370 and 372. Thus, the jaw assembly may not need to define a true single pivot point as is typical of hinge-type jaws known in the art. The pivotable action of the jaws along interface 370 may be described as a rolling pivot that optionally can allow for a degree of dynamic adjustment of the engagement gap g at the proximal end of the jaws. FIG. 11 illustrates one embodiment of the jaw 108 de-mated from the end effector 106. Referencing FIG. 11, the jaws elements 110, 108 can be retained relative to one another and the shaft 104 by means of protruding elements 375 that couples with arcuate slots 376 in an internal member 377 that is fixedly carried in bore 308 of shaft 104. Alternatively, outwardly protruding elements can cooperate with slots in the wall of shaft 104. Also, for example, the jaw assembly may (optionally) comprise springs for urging the jaws toward the open position, or closed position depending on the desired at-rest state of the device.

Figure 12:
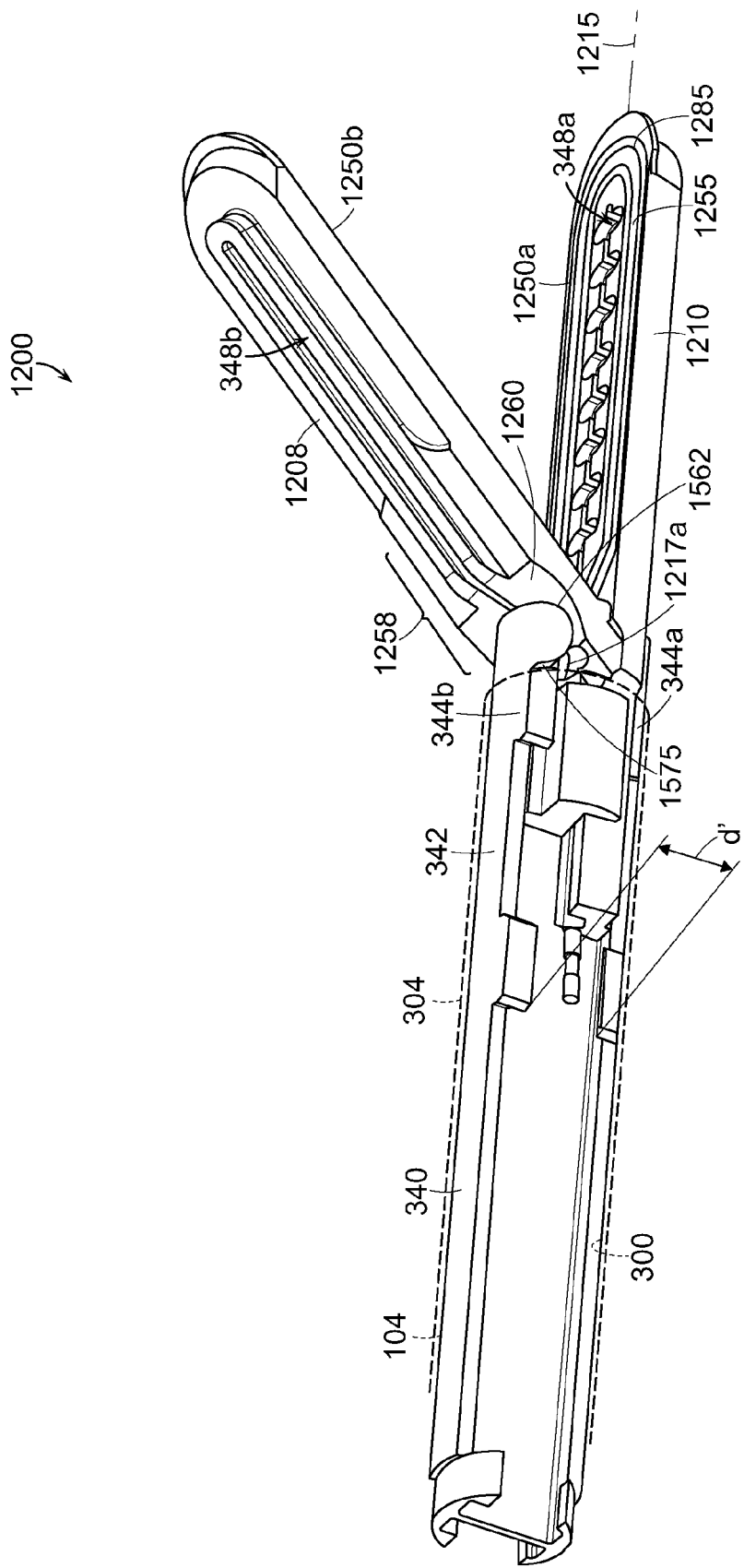
FIGS. 12-14 illustrate one embodiment of an end effector having a single rotating jaw member.
Figure 13:
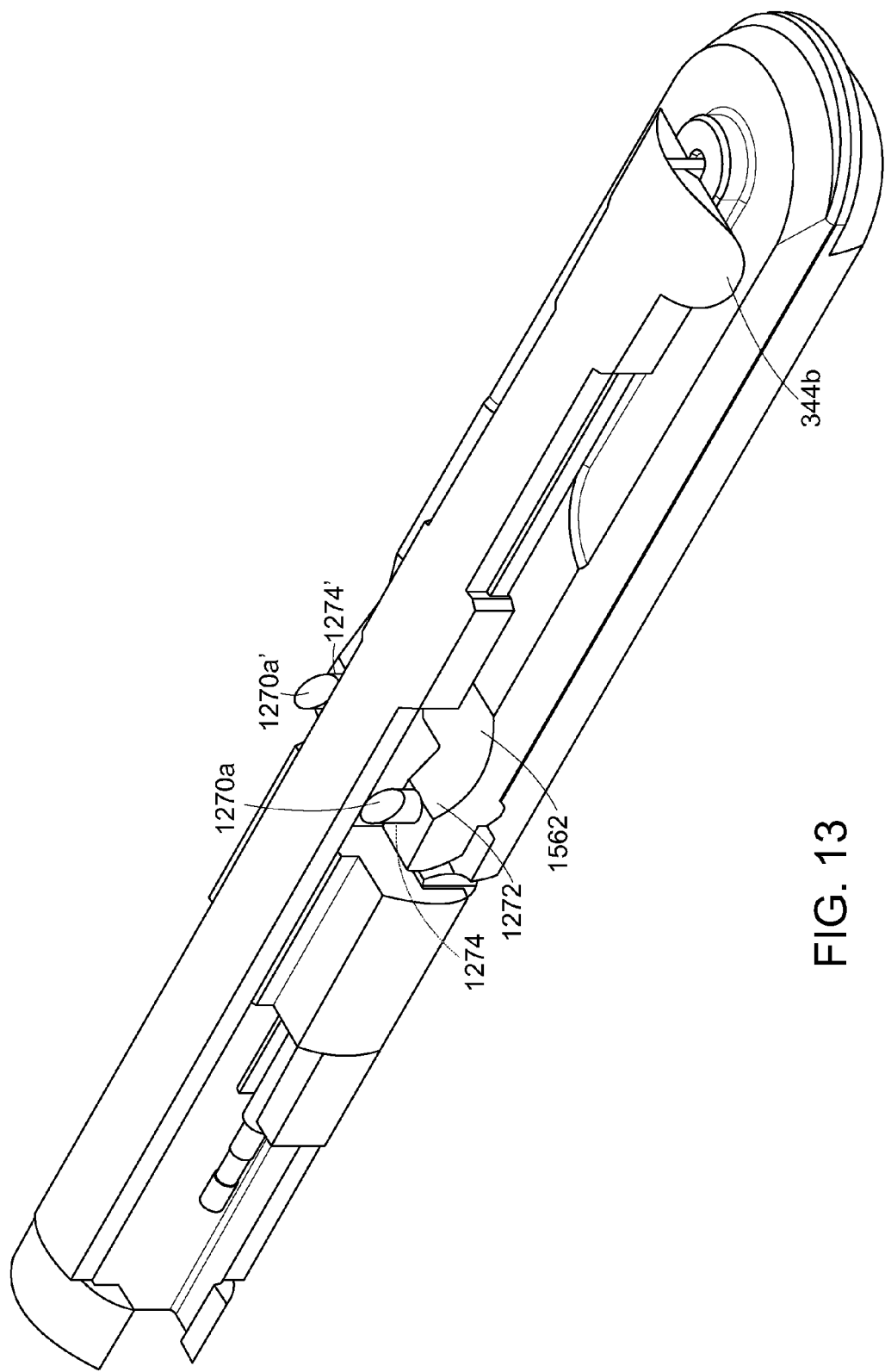

FIGS. 12-13 illustrate one embodiment of an end effector 1200 having a single rotating jaw member. Like the end effector 106 described above, the end effector 1200 is carried at the distal end 304 of the shaft 104 that has a bore 308 extending therethrough. According to various embodiments, the first (lower) jaw 1210 may be a fixed extension portion of the shaft 104. As can be seen in FIGS. 12 and 13, the second (upper) jaw 1208 is adapted to close or approximate along longitudinal axis 1215.

The opening-closing mechanism of end effector 1200 may provide cam surfaces for positive engagement between reciprocating member 340 and the jaws (i) for moving the jaws to a closed position to engage tissue under high compressive forces, and (ii) for moving the jaws toward the (first) open position thereby providing high opening forces to dissect tissue with outer surfaces of the jaw tips. The reciprocating member 340 operates as described previously to reciprocate within bore 308 of the shaft 104. As can be seen in FIG. 13, the distal end portion 342 of reciprocating member 340 carries distal first and second laterally-extending flange portions 344A and 344B with the blade-carrying transverse element 345 extending therebetween. The blade-carrying member slides within channels 348a and 348b in the jaws.

In the example embodiment of FIGS. 12 and 13, the first and second jaw members 1210 and 1208 again define engagement surfaces or planes 1250a and 1250b that deliver energy to engaged tissue. The engagement planes may carry one or more conductor/electrodes 1255 and, in various embodiments, may comprise a PTC matrix 1285 in at least one of the jaws' engagement surfaces 1250a and 1250b. In the embodiment of FIGS. 12 and 13, the upper jaw 1208 has a proximate end region 1258 that, in the open position, defines a first (proximally-facing) arcuate cam surface indicated at 1260 that is engaged by a first surface portion 1562 of the reciprocating member 340. The first (proximal) end region 1258 of the upper jaw, in the open position, further defines second (distally-facing) surface portions indicated at 1270a and 1270a' that are engaged by second surface 1272 of reciprocating member 340 for moving the jaw assembly to an open position.

Figure 14:
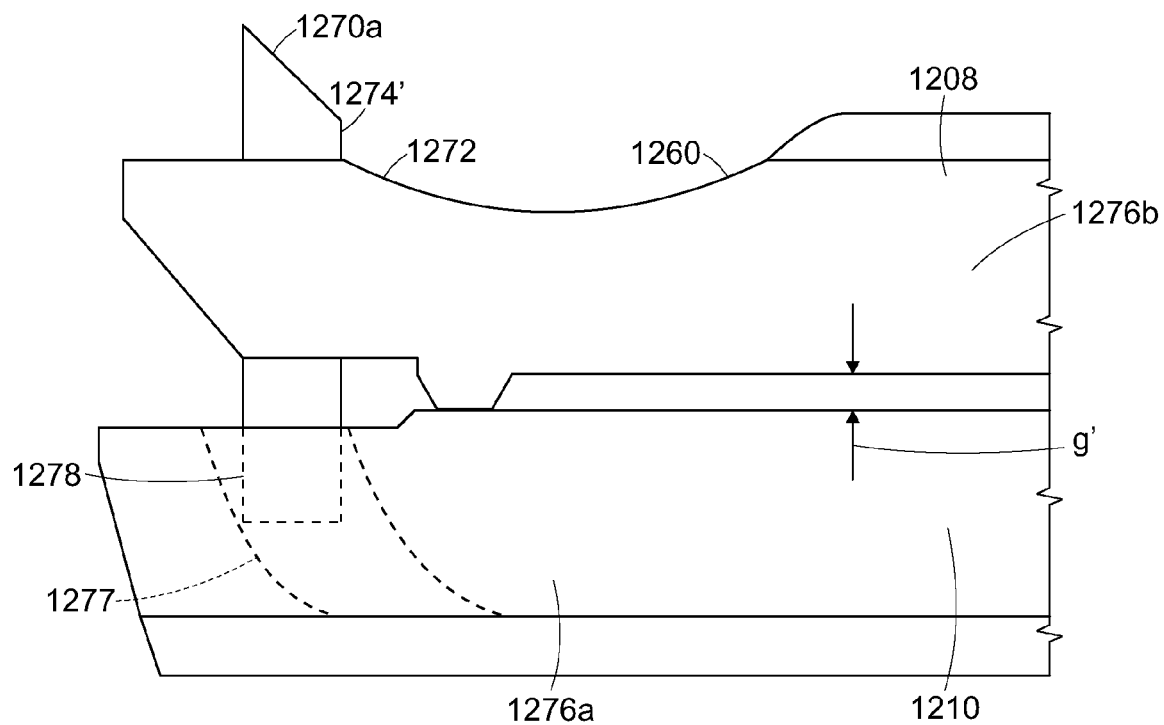

As can be seen best in FIG. 13, the cam surfaces 1270a and 1270a' may be formed into pins or projecting elements 1274 and 1274' that may serve multiple purposes. Referring to FIG. 14, the pins 1274 and 1274' extend through the upper jaw body 1276b and are received within arcuate bores 1277 in body 1276a of lower jaw 1210. The lower portions 1278 (collectively) of the pins 1274 and 1274' thus can retain upper jaw 1208 and prevent it from moving axially or laterally relative to the jaw axis 1215 while still allowing the jaw's rotation for opening and closing. The pin mechanism further allows for greatly simplified assembly of the instrument.

Figure 19:
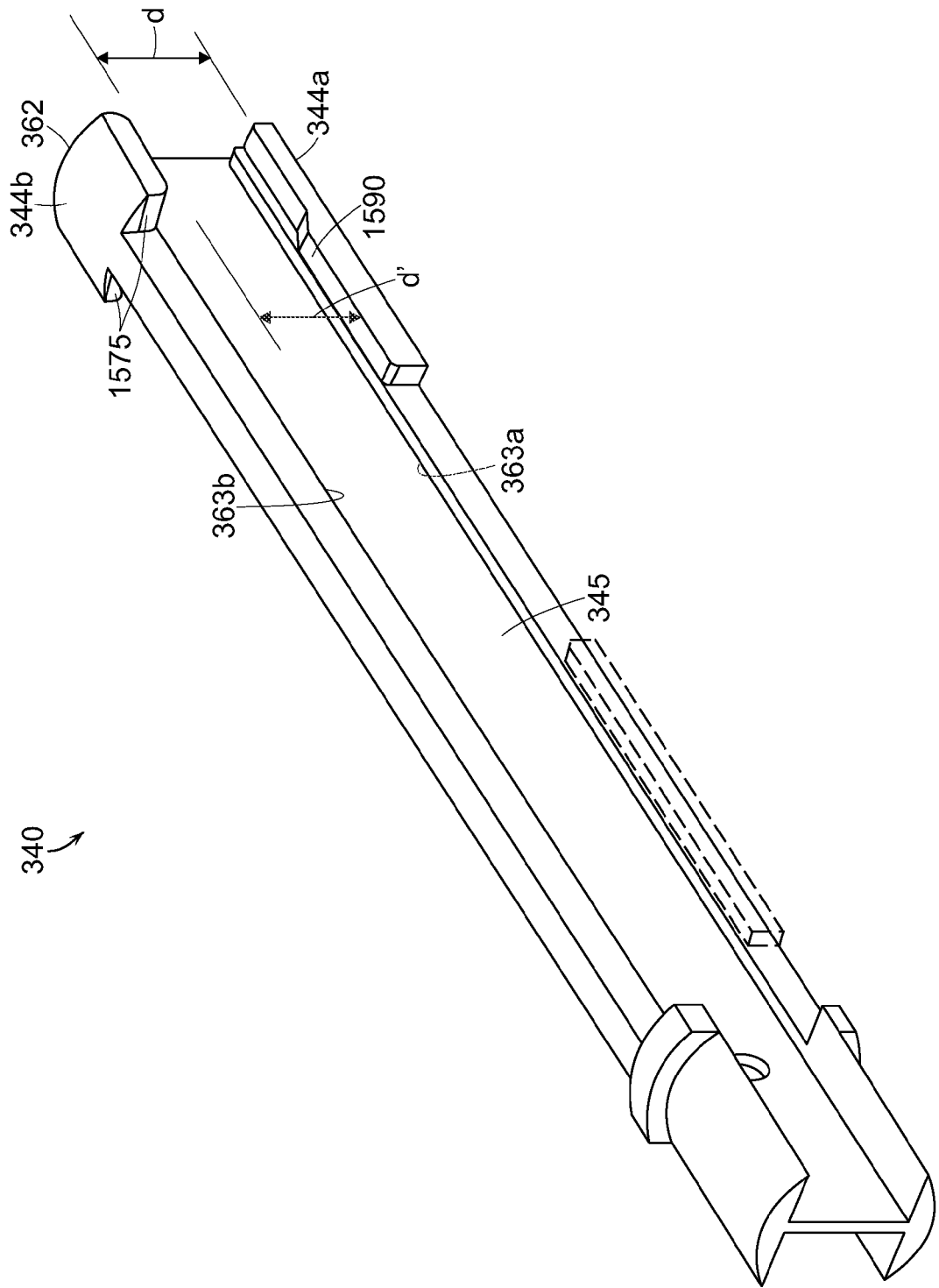
FIG. 19 illustrates one embodiment of the reciprocating member configured with separate elevated step or cam surfaces in the lower flange portions that are adapted to slidably engage the ends of the rectangular pins on either side of upper jaw.

The pins 1274 and 1274' may provide additional functionality by providing a degree of "vertical" freedom of movement within the first (proximal) end portion 1258 of the jaw. As can be seen in FIGS. 12 and 19, the distal laterally-extending flange portions 344A and 344B define a transverse dimension d (cf. FIG. 19) that in turn determines the dimension of the engagement gap g of the distal end of the jaws in the jaw-closed position (FIG. 14). The transverse dimension d equals the dimension between inner surfaces of flange portions 344A and 344B that slidably contact the outer surfaces of both jaws.

Figure 16:
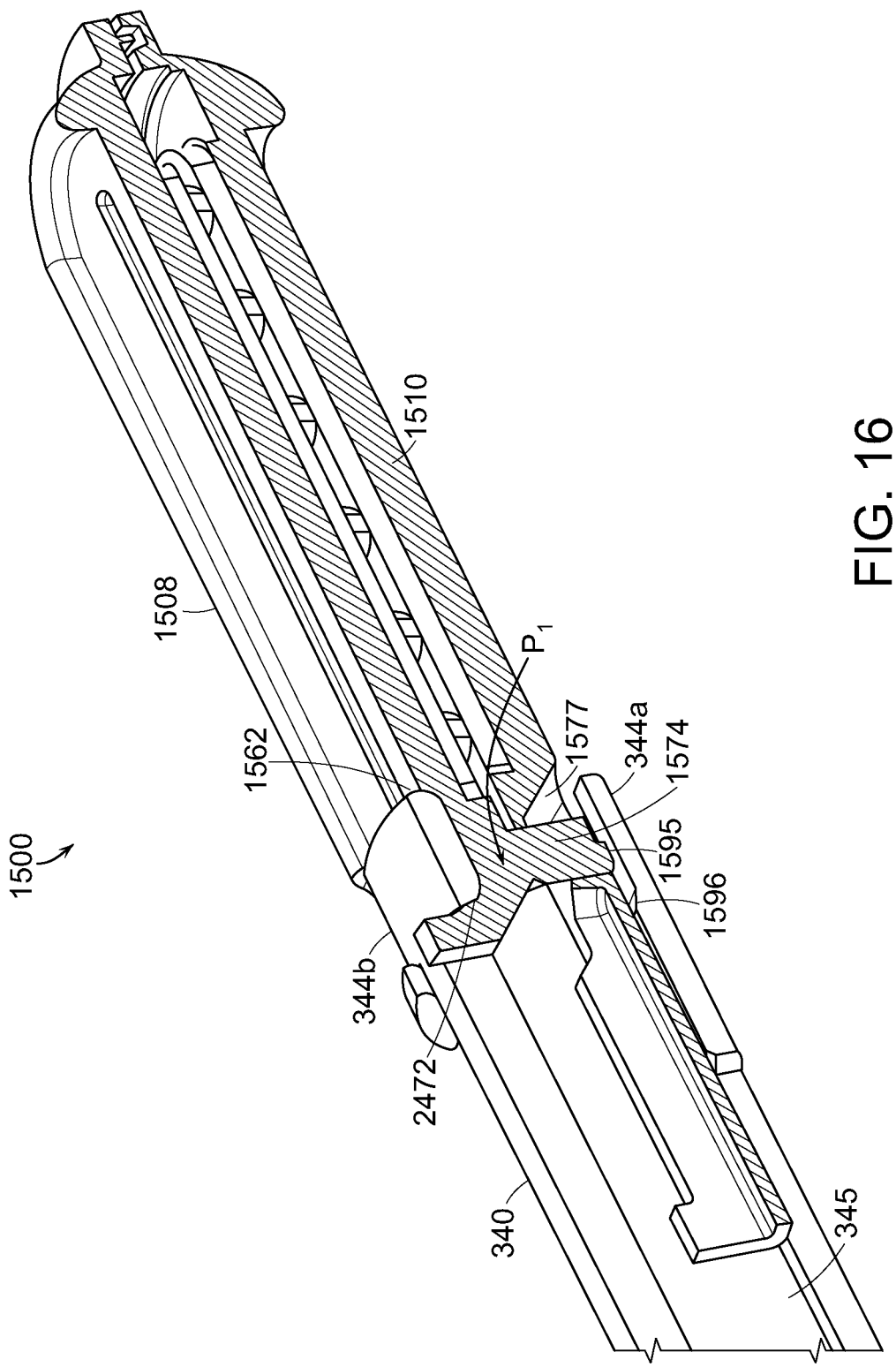
Figure 17:
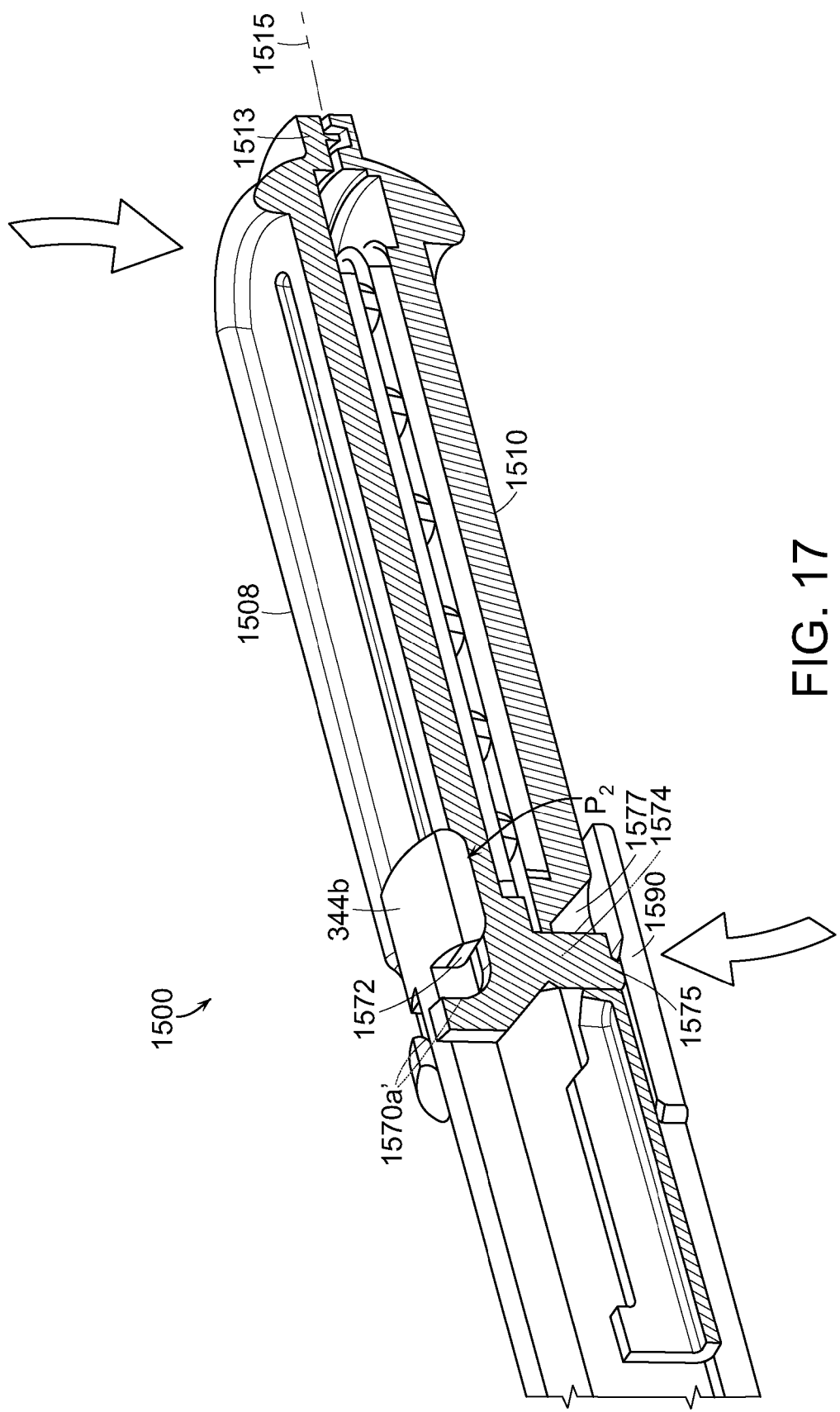
Figure 18:
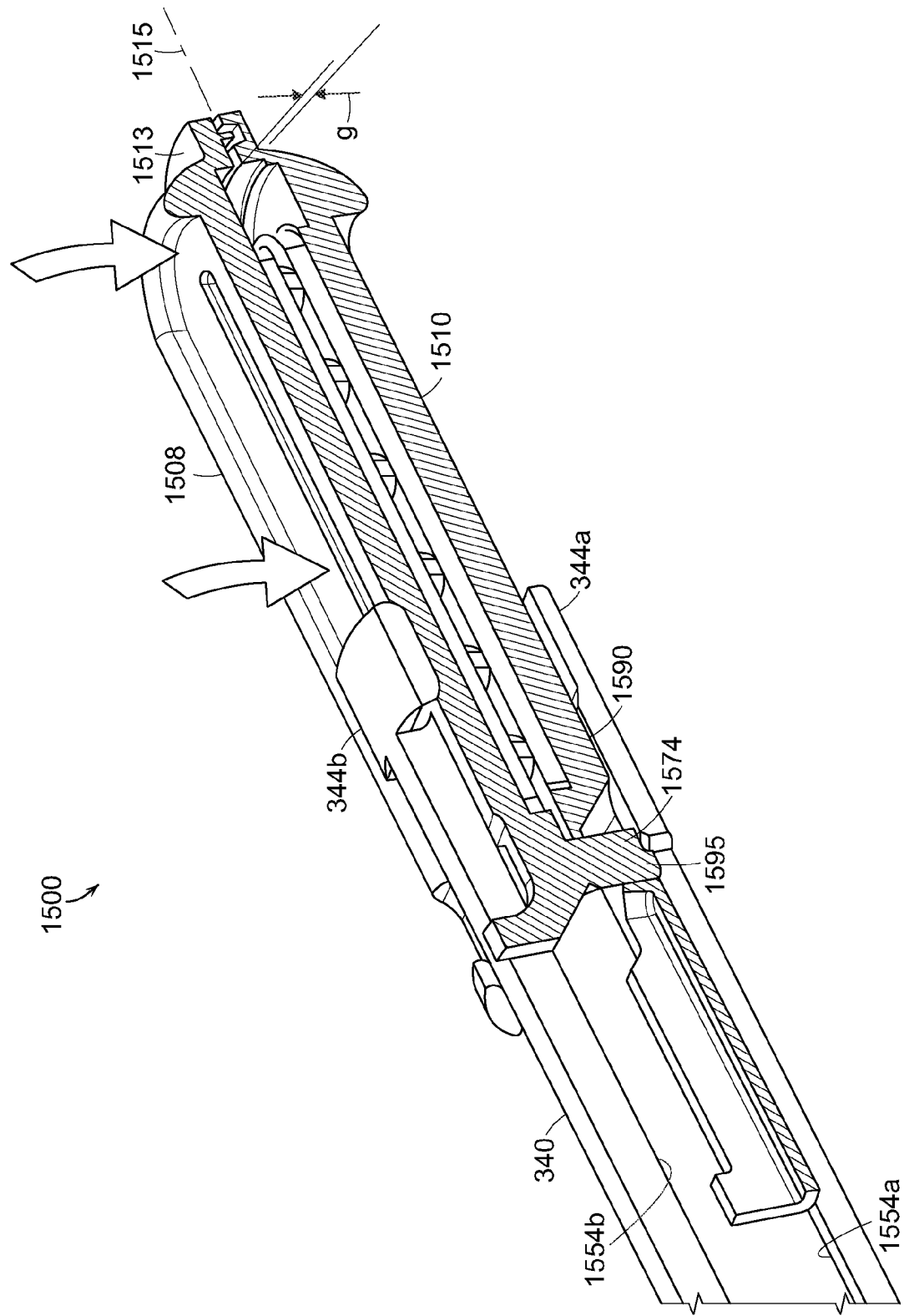

FIGS. 15-18 illustrate another embodiment of an end effector 1500 that provides both electrosurgical functionality and improved grasping and dissecting functionality for endoscopic surgeries. In FIGS. 15-18, both the upper and lower jaws are shown in cut-away views to show internal cam surfaces of the upper jaw 1510 and the reciprocating member 340. The jaw assembly 1500 may carry engagement surfaces for applying electrosurgical energy to tissue as in the previously described embodiments, as well as cutting means for transecting the engaged tissue volume. The jaw assembly 1500 relates to the ability of the jaw structure, in one mode of operation, to be used for general grasping and dissecting purposes wherein the distalmost tips 1513 of the jaws can close tightly on tissue with little movement of the actuator lever 113 in the handle of the instrument. At the same time, in another mode of operation, the jaw assembly 1500 can close to apply very high compressive forces on the tissue to enable welding. Thus, the jaw structure may provide (i) a first non-parallel jaw-closed position for grasping tissue with the distal jaws tips (FIG. 17), and (ii) a second parallel jaw-closed position for high compression of tissue for the application of electrosurgical energy (FIG. 18).

Figure 15:
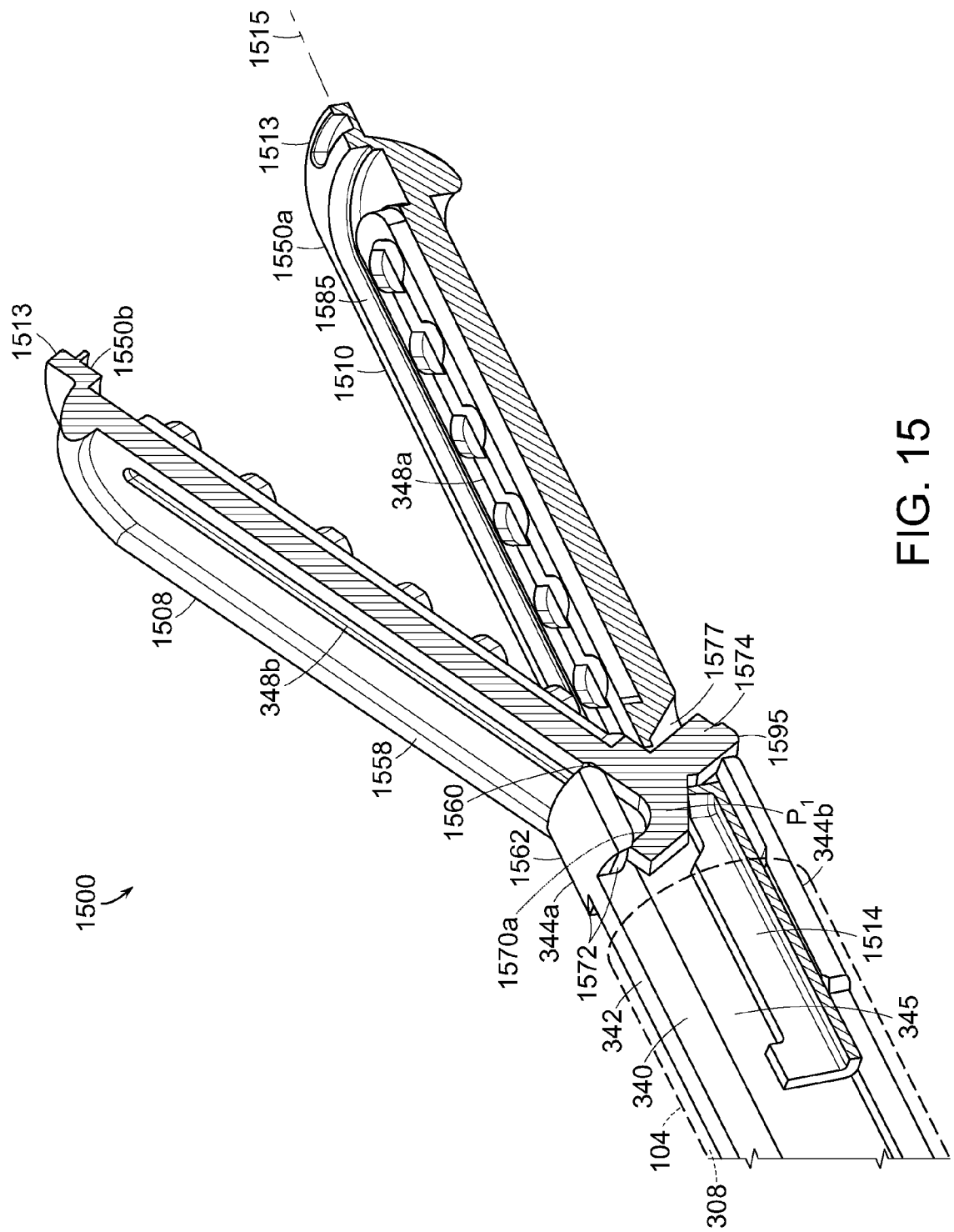
FIGS. 15-18 illustrate another embodiment of an end effector having a single rotating jaw member.

Referring to FIG. 15, the end effector 1500 again has a shaft 104 that is similar to the shaft 104 as used by the end effector 1200 with first (lower) jaw 1510 comprising a fixed extending portion 1514 of the shaft 104. As can be seen in FIG. 15, the second (upper) jaw 1508 is adapted to close or approximate about longitudinal axis 1515. The opening-closing mechanism of jaw assembly 1500 provides cam elements and cooperating jaw surfaces for positive engagement between the reciprocating member 340 as described previously (i) for moving the jaws to a closed position to engage tissue, and (ii) for moving the jaws toward the open position thereby providing high opening forces to dissect tissue with outer surfaces of the jaw tips 313.

The reciprocating member 340 (FIG. 19) operates as described previously to reciprocate within bore 308 of the shaft 104 (FIG. 15). As can be seen in FIG. 15, the distal end 342 of the reciprocating member 340 again carries distal flange portions 344A and 344B with a blade-carrying transverse portion 345 therebetween. The transverse portion 345 slides within channels 348a and 348b in the paired jaws. In the example embodiment of FIG. 15, the first and second jaws 1510 and 1508 again define engagement surfaces 1550a and 1550b that can deliver electrosurgical energy to engaged tissue.

In the embodiment of FIG. 15, the upper jaw 1508 has a proximal end 1558 that defines a first (proximally-facing) arcuate jaw surface 1560 that is engaged by a first cam surface element 1562 of reciprocating member 340 for opening the jaw. The proximal end 1558 of the upper jaw further defines second (distally-facing) jaw surface portions indicated at 1570a and 1570a' that are engaged by second cam element 1572 of reciprocating member 340 for moving the jaw assembly to an open position.

The embodiment of FIG. 15 shows that the upper jaw 1508 has a floating primary pivot location indicated at $P_1$ that is provided by the projecting elements or rectangular pins 1574 (collectively) on either side of the channel portions 348a that slidably extend into bores 1577 (collectively) in the lower jaw body (cf. Figure Z3). The lower portions of the pins 1574 thus allow upper jaw 1508 to rotate while at the same time the pin-and-bore mechanism allows the upper jaw to move upwardly away from the lower jaw.

For example, the degree of "vertical" freedom of movement of the upper jaw allows for the system to "tilt" the distal tip 1513 of upper jaw 1508 toward the axis 1515 to thereby allow the distal jaw tips 1513 to grasp tissue. This is termed a non-parallel closed position herein. The tilting of the jaw is accomplished by providing a plurality of cam surfaces in the upper jaw 1508 and the reciprocating member 340.

As can be seen in FIGS. 15 and 19, the lower and upper laterally-extending flange portions 344A and 344B of the reciprocating member 340 define a transverse dimension d that determines the dimension of gap g between the engagement surface of the jaws in the fully jaw-closed position (FIG. 18). The transverse dimension d equals the dimension between inner surfaces of flange portions 344A and 344B that slidably contact the outer surfaces of both jaws.

FIG. 19 illustrates one embodiment of the reciprocating member 340 configured with separate elevated step or cam surfaces 1590 in the lower flange portions 344A that are adapted to slidably engage the ends 1595 of the rectangular pins 1574 on either side of upper jaw 1508. The elevated cam surfaces 1590 of reciprocating member 340 thus create another transverse dimension d' between inner surfaces of the flange portions 344A and 344B that move the jaws toward either the first jaw-closed position or the second jaw-closed position.

Now turning to FIGS. 15-18, the sequence of cut-away views illustrate how the multiple cam surfaces cause the jaws to move between a first "tilted" jaw-closed position to a second "high-compression" jaw-closed position. In FIG. 15, the jaws are in an open position. In FIG. 16, the reciprocating member 340 is moved distally and its cam surface element 1562 pushes on jaw surfaces 1560 to move the jaws toward a closed position wherein the jaws rotate about primary pivot location $P_1$. In FIG. 16, it can be seen that the elevated cam surfaces 1590 in the lower flange 344A have not yet engaged the ends 1595 of the rectangular pins 1574.

Now turning to FIG. 17, the reciprocating member 340 is moved further distally wherein the elevated cam surfaces 1590 of lower flange 344A have now engaged and elevated the ends 1595 of rectangular pins 1574 thereby tilting the upper jaw. The upper jaw 1508 is tilted slightly by forces in the direction of the arrows in FIG. 17 as the upper flange 1544B holds the upper jaw 1508 at a secondary pivoting location indicated at $P_2$—at the same time that the step of the cam surface element 1590 lifts the pins 1574 and the proximal portion 1558 of the upper jaw 1508 upward.

Thus, the system functions by providing a slidable cam mechanism for lifting the proximal end of the jaw while maintaining the medial jaw portion in a fixed position to thereby tilt the distal jaw to the second jaw-closed position, with the pivot occurring generally about secondary pivot $P_2$ which is distal from the primary pivot location $P_1$.

FIG. 18 next shows the reciprocating member 340 moved further distally wherein the elevated cam surfaces 1590 of lower flange 344A slides distally beyond the ends 1595 of rectangular pins 1574 thus causing the flanges 344A and 344B together with the trailing edge portions 1575 of the "I"-beam portion (FIG. 19) of the member 340 to apply very high compression forces over the entire length of the jaws as indicated by the arrows in FIG. 18. This position is termed a parallel jaw-closed position herein. Another advantage is that the jaw structure is in a "locked" position when the reciprocating member 340 is fully advanced.

Figure 20:
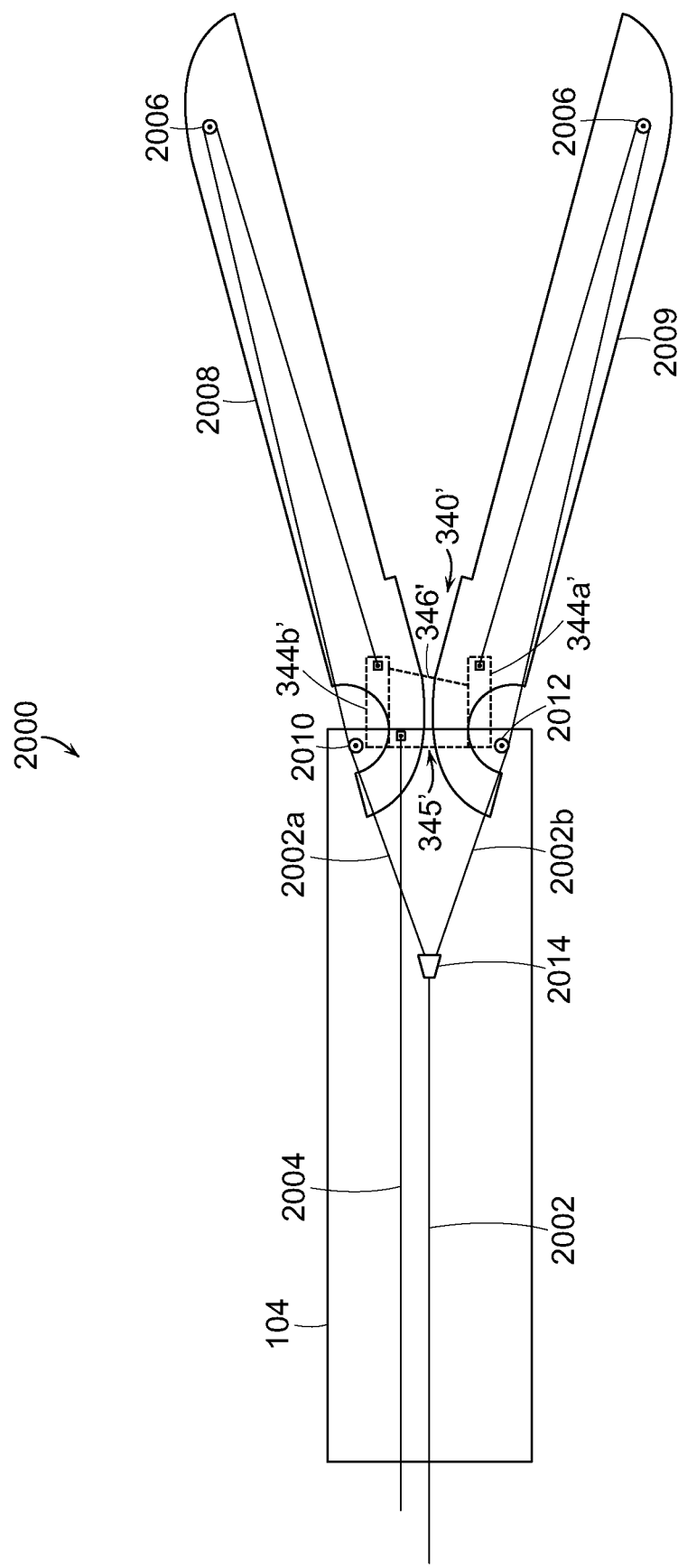
FIGS. 20-22 illustrates a cable-actuated embodiment of the end effector shown in FIG. 3.
Figure 21:
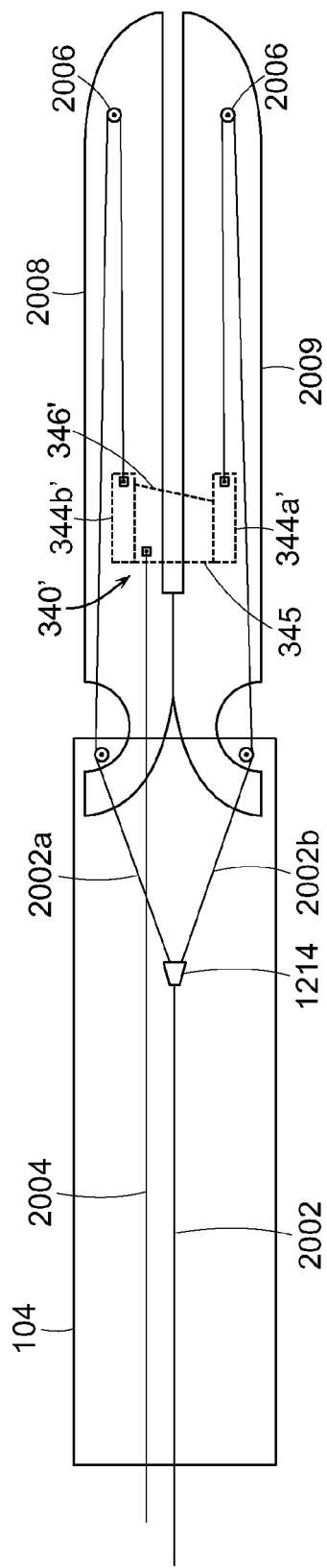
Figure 22:
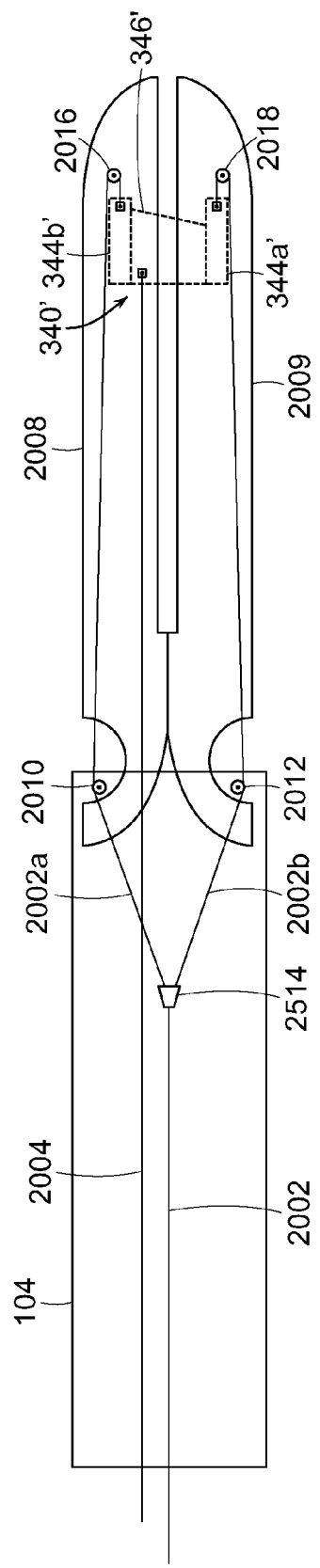

FIGS. 20-22 illustrates a cable-actuated embodiment of the end effector 2000. The end effector 2000 may comprise jaw members 2008, 2009 and shaft 104 as described above. The jaw members 2008, 2009 may be pivotally coupled to one another in any suitable manner. For example, proximal portions of the jaw members 2008, 2009 may rollably contact one another to cause the members 2008, 2009 to open and close, as described above. In various embodiments, the jaw members 2008, 2009 may be pivotally coupled at a clevis with a pin or other mechanical pivot device (not shown). A cable driven reciprocating member 340' may operate in a manner similar to member 340 described above. The member 340' may comprise a transverse element 345' and a pair of flanges 344A' and 344B'. The member 340' may be driven by a pair of cables 2002 and 2004. The cables 2002, 2004 may be made from any suitable material including, for example, a tri-layered steel cable. The cable 2004 may be pulled proximally to pull the member 340' proximally and open the jaw members 2008, 2009, as shown in FIG. 20.

The cable 2002 may be pulled proximally to close the jaw members 2008, 2009. At a splitter, 2014, the cable 2002 may be split into two cables 2002a and 2002b. 2002a may be routed by one or more pulleys 2010 through an interior portion of the jaw member 2008. An additional pulley 2006, located at a distal portion of the jaw member 2008, may re-route the cable 2002a back through the jaw member 2008 to the member 340'. The pulleys 2010, 2006 may be any suitable devices configured to route the direction of the cable 2002 without exerting an excessive frictional force. For example, the pulleys 2010, 2006 may comprise rotating wheel members or may, in various embodiments, comprise rotatable or stationary posts or pegs around which the cable 2002 is wrapped. The stationary posts or pegs could be a dual-purpose component and may, for example, serve as a support to the jaw members 2008, 2009. According to various embodiments, a low-friction coating material such as VECTRAN may be applied to the post and/or the cable 2002.

Pulling the cable 2002 proximally (e.g., exerting a proximally directed force on the cable 2002) may cause the respective cables 2002a, 2002b to pull the member 340' distally, closing the jaw members 2008, 2009, as described above with respect to FIGS. 7 and 8. For example, flanges 344A' and 344B' may contact surfaces 330A and 330B of the respective jaw members 2009, 2008, causing the jaw to transition into the closed position shown in FIG. 21. After the jaw members 2008, 2009 are in the closed position, continued exertion of proximal force on the cable 2002 may cause the member 340' to traverse the jaw members 2008, 2009 via respective channels 348b, 348a (FIGS. 4 and 11), as shown in FIGS. 20 and 22. As illustrated in FIGS. 20-22, the flanges 344A' and 344B' ride within the respective jaw members 2008, 2009 instead of outside the jaw members 2008, 2009, as shown in FIGS. 3-4 and 7-8. It will be appreciated that either configuration may be used.

To open the jaw members 2008, 2009, the cable 2004 may be pulled proximally. This may, in turn, return the member 340' to the position shown in FIG. 20. The jaw members 2008, 2009 may be spring-biased to the open position shown in FIG. 20. Alternatively, or in addition, the member 340' may act on the jaw members 2008, 2009 to cause them to open, for example, as described above with respect to FIGS. 7 and 8.

FIGS. 23-25 illustrate one embodiment of an end effector 2300 having a cable-operated moving jaw member 2302 and a stationary jaw member 2304. According to various embodiments, the stationary jaw member 2304 may be fastened to the shaft 104. The moving jaw member 2302 may be pivotally coupled to the stationary jaw member 2304, allowing the jaw members 2302, 2304 to transition from the open position shown in FIG. 23 to the closed position shown in FIGS. 22 and 24. For example, the moving jaw member 2302 may be coupled to the stationary jaw member 2304 about a pivot pin 2306. According to other various embodiments, the moving jaw member 2302 may be coupled in a manner similar to that of the jaw member 1208 of the end effector 1200 described above such that the jaw member 1208 defines a rolling pivot point.

In use, the end effector 2000 may be transitioned to the closed position by exerting a proximally directed force on the cable 2002. The cable 2002 may be routed by pulleys 2308, 2310 and 2320 to exert a distally directed force on the member 2306. This may, initially, cause the moving jaw member 2302 to close against the stationary jaw member 2304, as described above. After the jaw members 2302, 2304 are in the closed position, the member 340' may traverse the jaw members 2302, 2304 as illustrated in FIGS. 24-25. As described above, this may increase a compressive force on tissue that may be between the jaw members 2302, 2304. In addition, the leading edge 346' of the member 340' may transect the tissue, as described. To open the jaw members, a proximally directed force may be exerted on cable 2002. This may cause the member 340' to translate proximally within the jaw members 2302, 2304, returning to the position shown in FIG. 23. The jaw members 2302, 2304 may then be opened according to any suitable manner. For example, the jaw members 2302, 2304 may be biased to the open position by a spring (not shown). Also, for example, the member 340', as it translates proximally, may exert a force on the moving jaw member 2302 tending to cause it to pivot open. This may occur in a manner similar to that described above with respect to FIGS. 3-4 and 7-8.

According to various embodiments, the cable-driven end effectors 2000 and 2300 shown in FIGS. 20-25 may provide certain advantages. For example, as illustrated, the respective jaw members are both opened and closed by a proximally directed force. This may make it easier for the shaft 104 to be flexible and/or articulatable. For example, FIG. 26 illustrates one embodiment of the end effector 2300 installed on a shaft 104 comprising an articulation pivot 2602. The articulation pivot 2602 may be actuated in any suitable manner known in the art. As illustrated, the articulation pivot 2602 may comprise a pulley and/or routing post 2604 that may route one or both of the cables 2002, 2004 through the pivot 2602. Because the jaw members are both opened and closed by a proximally directed force, the cables 2002, 2004 may be placed in tension, rather than compression. This may avoid mechanical problems associated with trying to direct a compressive force around a pivot.

FIGS. 25a-25b illustrate one embodiment of an end effector 2500 with separately actuatable closure and cutting. The end effector 2500 may comprise a pair of rotatable jaw members 2502, 2504. It will be appreciated, however, that in various embodiments, only one of the jaws may be rotatable, for example, similar to the embodiments shown in FIGS. 23-25. Referring back to FIG. 25a, the end effector 2500 may comprise a slidable collar 2516, which may translate distally to close the jaw members 2502, 2504 and provide a compressive force tending to hold the jaw members 2502, 2504 closed. The collar 2516 is shown in cross-section in FIGS. 25a and 25b. According to various embodiments, the collar 2516 may be advanced distally from the position shown in FIG. 25a to transition the jaw members 2502, 2504 to the closed position shown in FIG. 25b with a cable 2508. The cable 2508 may break into two branches 2508a, 2508b at junction 2518. The respective branches 2508a, 2508b of the cable 2508 may be routed by pulleys 2512a, 2512b and 2514a, 2514b and may, ultimately, be coupled the collar 2516. When the cable 2508 is translated proximally, for example, in response to the motion of an actuator 113 or other trigger mechanism, the collar 2516 may be pulled distally, as shown in FIG. 25b.

To open the end effector 2500 (e.g., to transition from the position shown in FIG. 25b to the position shown in FIG. 25a), a second cable 2506 may be pulled proximally. Again, the cable 2506 may be pulled proximally by the motion of an actuator 113 or other trigger mechanism. Similar to the cable 2508, the cable 2506 may be split into branches 2506a and 2506b at junction 2520. The branches 2506a, 2506b may be coupled to a proximal portion of the collar 2516. Proximal motion of the cable 2506, for example, as the result of the motion of an actuator 113, may pull the collar proximally from the position shown in FIG. 25b to the position shown in FIG. 25a. In the end effector 2500, the reciprocating member 340" may extend proximally to the shaft 104 to an actuator, such as the actuator 113. The reciprocating member may be actuatable separately from the collar 2516. For example, the reciprocating member 340" and its cutting edge 346' may be extended distally to cut tissue either at the same time that the collar 2516 is advancing to close the jaw members 2502, 2504, or at a later time.

According to various embodiments, the end effectors 106, 1200, 2000 and 2300 may be used to cut and fasten tissue utilizing electrical energy. The examples described below are illustrated with the end effector 106. It will be appreciated, however, that similar configurations and techniques may be used with the end effectors 2000 and 2300 described above. Referring to the end effector 106 shown in FIGS. 3-4 and 7-8, the electrodes 120, 122 of the end effector 106 may be arranged in any suitable configuration. In use, for example, tissue (not shown) may be captured between the jaw members 2008, 110. RF current may flow across the captured tissue between the opposing polarity electrodes 120, 122. This may serve to join the tissue by coagulation, welding, etc. The RF current may be activated according to any suitable control method. For example, according to various embodiments, the electrodes 120, 122 may be used to implement a "power adjustment" approach, a "current-path directing" approach or an approach referred to herein as a "weld" or "fusion" approach. These various approaches are illustrated herein with reference to FIGS. 27-30, which show the walls of an example blood vessel acted upon by various RF end effectors including those using the power adjustment and current-path directing approaches from above.

FIG. 27 shows an example embodiment of a vessel having opposing wall portions 2a and 2b. FIG. 28 is a graphic illustration of one embodiment of the opposing vessel walls portions 2a and 2b with the tissue divided into a grid with arbitrary micron dimensions. For example, the grid may represent 5 microns on each side of the targeted tissue. In order to coagulate or weld tissue, collagen and other protein molecules within an engaged tissue volume may be denatured by breaking the inter- and intra-molecular hydrogen bonds. When heat or other energy is removed (e.g., thermal relaxation), the molecules are re-crosslinked to create a fused-together tissue mass. It is desirable that each micron-dimensioned volume of tissue be elevated to the temperature needed to denature the proteins therein in a substantially uniform manner.

Failing to heat tissue portions in a uniform manner can lead to ohmic heating, which can create portions of tissue that are not effectively joined and reduce the strength of the joint. Non-uniformly denatured tissue volume may still be "coagulated" and can prevent blood flow in small vasculature that contains little pressure. However, such non-uniformly denatured tissue may not create a seal with significant strength, for example in 2 mm to 10 mm arteries that contain high pressures. It is often difficult to achieve substantially uniform heating with a bipolar RF device in tissue, whether the tissue is thin or thick. For example, as RF energy density in tissue increases, the tissue surface tends to become desiccated and resistant to additional ohmic heating. Localized tissue desiccation and charring can sometimes occur almost instantly as tissue impedance rises, which then can result in a non-uniform seal in the tissue. Also, many RF jaws cause further undesirable effects by propagating RF density laterally from the engaged tissue thus causing unwanted collateral thermal damage.

To achieve substantially uniform coagulation, various embodiments described herein may utilize a "power adjustment" approach, a "current-path directing" approach and/or an approach referred to herein as a "weld" or "fusion" approach. According to the "power adjustment" approach, the RF generator 124 can rapidly adjust the level of total power delivered to the jaws' engagement surfaces in response to feedback circuitry, which may be present within the generator 124 and/or at the end effector 106, and may be electrically coupled to the active electrodes. The feedback circuitry may measure tissue impedance or electrode temperature. FIG. 29 illustrates one embodiment of the blood vessel of FIG. 27 acted upon by a device implementing a "power adjustment" approach to energy delivery. Opposing vessel walls 2a and 2b are shown compressed with cut-away phantom views of opposing polarity electrodes 2902, 2904 on either side of the tissue. For example, the electrode 2902 may be positioned on one jaw member 2008, 110, while the electrode 2904 may be positioned on the opposite jaw member. One advantage of such an electrode arrangement is that 100% of each jaw engagement surface comprises an "active" conductor of electrical current—thus no tissue is engaged by an insulator which theoretically would cause a dead spot (no ohmic heating) proximate to the insulator.

FIG. 29 also graphically depicts current paths p in the tissue at an arbitrary time interval that can be microseconds (μs) apart. Such current paths p would be random and constantly in flux—along transient most conductive pathways through the tissue between the opposing polarity electrodes. The thickness of the paths is intended to represent the constantly adjusting power levels. Typically, the duration of energy density along any current path p is on the order of microseconds and the thermal relaxation time of tissue is on the order of milliseconds. Instruments using the power adjustment approach may be useful for sealing relatively small vessels with relatively low fluid pressure. This is because, given the spatial distribution of the current paths and the dynamic adjustment of their power levels, it is unlikely that enough random current paths will revisit and maintain each discrete micron-scale tissue volume at the targeted temperature before thermal relaxation. Also, because the hydration of tissue is constantly reduced during ohmic heating—any region of more desiccated tissue will lose its ohmic heating, rendering it unable to be "welded" to adjacent tissue volumes.

In a second "current-path directing" approach, the end effector jaws carry an electrode arrangement in which opposing polarity electrodes are spaced apart by an insulator material, which may cause current to flow within an extended path through captured tissue rather than simply between surfaces of the first and second jaws. "Current-path directing" techniques are also used to improve the quality of energy-delivered seals. FIG. 30 illustrates one embodiment of the blood vessel of FIG. 27 acted upon by a device implementing a current-path directing approach to energy delivery. In FIG. 30, vessel walls 2a and 2b are engaged between opposing jaws surfaces with cut-away phantom views of electrodes 3002, 3004, 3006, 3008, with opposing polarity (+) and (−) electrodes (3002, 3004 and 3006, 3008) on each side of the engaged tissue. For example, electrodes 3002 and 3004 may be positioned on one of the jaw members 2008, 110 while electrodes 3006 and 3008 maybe positioned on the opposite electrode. An insulator 3010 is shown in cut-away view that electrically isolates the electrodes in the jaw. The tissue that directly contacts the insulator 3010 will only be ohmically heated when a current path p extends through the tissue between the spaced apart electrodes. FIG. 30 graphically depicts current paths p at any arbitrary time interval, for example in the μs range. Again, such current paths p will be random and in constant flux along transient conductive pathways.

A third approach, according to various embodiments, may be referred to as a "weld" or "fusion" approach. The alternative terms of tissue "welding" and tissue "fusion" are used interchangeably herein to describe thermal treatments of a targeted tissue volume that result in a substantially uniform fused-together tissue mass, for example in welding blood vessels that exhibit substantial burst strength immediately post-treatment. Such welds may be used in various surgical applications including, for example, (i) permanently sealing blood vessels in vessel transection procedures; (ii) welding organ margins in resection procedures; (iii) welding other anatomic ducts or lumens where permanent closure is desired; and also (iv) for performing vessel anastomosis, vessel closure or other procedures that join together anatomic structures or portions thereof.

The welding or fusion of tissue as disclosed herein may be distinguished from "coagulation", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "welding" as the term is used herein. Such surface coagulation does not create a weld that provides any substantial strength in the treated tissue.

A "weld," for example, may result from the thermally-induced denaturation of collagen and other protein molecules in a targeted tissue volume to create a transient liquid or gel-like proteinaceous amalgam. A selected energy density may be provided in the targeted tissue to cause hydrothermal breakdown of intra- and intermolecular hydrogen crosslinks in collagen and other proteins. The denatured amalgam is maintained at a selected level of hydration—without desiccation—for a selected time interval, which may be very brief. The targeted tissue volume may be maintained under a selected very high level of mechanical compression to insure that the unwound strands of the denatured proteins are in close proximity to allow their intertwining and entanglement. Upon thermal relaxation, the intermixed amalgam results in protein entanglement as re-crosslinking or renaturation occurs to thereby cause a uniform fused-together mass.

To implement the welding described above, the electrodes 120, 122 (or electrodes that are part of the other end effector embodiments described herein) may, one or both, comprise an electrically conductive portion and a portion comprising a positive temperature coefficient (PTC) material having a selected increased resistance that differs at selected increased temperatures thereof. The PTC material may be positioned between the electrically conductive portion and any tissue to be acted upon by the end effector 106. One type of PTC material is a ceramic that can be engineered to exhibit a selected positively slope curve of temperature-resistance over a temperature range of about 37° C. to 100° C. Another type of PCT material may comprise a polymer having similar properties. The region at the higher end of such a temperature range brackets a targeted "thermal treatment range" at which tissue can be effectively welded. The selected resistance of the PTC matrix at the upper end of the temperature range may substantially terminate current flow therethrough.

In operation, it can be understood that the electrode 120 or 122 will apply active RF energy (ohmic heating within) to the engaged tissue until the point in time that the PTC matrix is heated to exceed the maximum of the thermal treatment range. Thereafter, RF current flow from the engagement surface will be lessened—depending on the relative surface areas of the first and second electrodes 120, 122. This instant and automatic reduction of RF energy application may prevent any substantial dehydration of tissue proximate to the engagement plane. By thus maintaining an optimal level of moisture around the engagement plane, the working end can more effectively apply energy to the tissue—and provide a weld thicker tissues with limited collateral thermal effects.

In various embodiments, surgical instruments utilizing various embodiments of the transection and sealing instrument 100, with the various end effectors and actuating mechanisms described herein may be employed in conjunction with a flexible endoscope. FIG. 31 illustrates one embodiment of an endoscope 3114 (illustrated here as a gastroscope) inserted into the upper gastrointestinal tract of a patient. The endoscope 3114 may be any suitable endoscope including, for example, the GIF-100 model available from Olympus Corporation. The endoscope 3114 has a distal end 3116 that may include various optical channels, illumination channels, and working channels. According to various embodiments, the endoscope 3114 may be a flexible endoscope.

FIG. 32 illustrates one embodiment of a distal portion 3116 of the endoscope 3114, which may be used with the transection and sealing instrument 100 described herein. The example endoscope 3114 shown comprises a distal face 3104, which defines the distal ends of illumination channels 3108, an optical channel 3106 and a working channel 3110. The illumination channels 3108 may comprise one or more optical fibers or other suitable waveguides for directing light from a proximally positioned light source (not shown) to the surgical site. The optical channel 3106 may comprise one or more optical fibers or other suitable waveguides for receiving and transmitting an image of the surgical site proximally to a position where the image may be viewed by the clinician operating the endoscope 3114. As described above, the working channel 3110 may allow the clinician to introduce one or more surgical tools to the surgical site. Examples of such surgical tools include scissors, cautery knives, suturing devices, and dissectors. It will be appreciated that the endoscope 3114 is but one example of an endoscope that may be used in accordance with various embodiments. Endoscopes having alternate configurations of optical channels 3106, illumination channels 3108 and/or working channels 3110 may also be used. According to various embodiments, the endoscope 3114 may be, or may be used in conjunction with, steerable devices such as traditional flexible endoscopes or steerable overtubes as described in U.S. Patent Application Publication No. 2010/0010299, incorporated herein by reference. Combinations of flexible endoscopes and steerable overtubes may also be used in some embodiments.

In at least one such embodiment, the endoscope 3114, a laparoscope, or a thoracoscope, for example, may be introduced into the patient trans-anally through the colon, the abdomen via an incision or keyhole and a trocar, or trans-orally through the esophagus or trans-vaginally through the cervix, for example. These devices may assist the clinician to guide and position the transection and sealing instrument 100 near the tissue treatment region to treat diseased tissue on organs such as the liver, for example.

In one embodiment, Natural Orifice Translumenal Endoscopic Surgery (NOTES)™ techniques may be employed to introduce the endoscope 3114 and various instruments into the patient and carry out the various procedures described herein. A NOTES™ technique is a minimally invasive therapeutic procedure that may be employed to treat diseased tissue or perform other therapeutic operations through a natural opening of the patient without making incisions in the abdomen. A natural opening may be the mouth, anus, and/or vagina. Medical implantable instruments may be introduced into the patient to the target area via the natural opening. In a NOTES™ technique, a clinician inserts a flexible endoscope into one or more natural openings of the patient to view the target area, for example, using a camera. During endoscopic surgery, the clinician inserts surgical devices through one or more lumens or working channels of the endoscope 3114 to perform various key surgical activities (KSA). These KSAs include forming an anastomosis between organs, performing dissections, repairing ulcers and other wounds. Although the devices and methods described herein may be used with NOTES™ techniques, it will be appreciated that they may also be used with other surgical techniques including, for example, other endoscopic techniques, and laparoscopic techniques.

It will be appreciated that the terms "proximal" and "distal" are used herein with reference to a clinician manipulating an end of an instrument extending from the clinician to a surgical site (e.g., through a trocar, through a natural orifice or through an open surgical site). The term "proximal" refers to the portion closest to the clinician, and the term "distal" refers to the portion located away from the clinician. It will be further appreciated that for conciseness and clarity, spatial terms such as "vertical," "horizontal," "up," and "down" may be used herein with respect to the drawings. However, surgical instruments are used in many orientations and positions, and these terms are not intended to be limiting and absolute.

While several embodiments have been illustrated and described, and while several illustrative embodiments have been described in considerable detail, the described embodiments are not intended to restrict or in any way limit the scope of the appended claims to such detail. Additional advantages and modifications may readily appear to those skilled in the art. Those of ordinary skill in the art will readily appreciate the different advantages provided by these various embodiments.

While several embodiments have been described, it should be apparent, however, that various modifications, alterations and adaptations to those embodiments may occur to persons skilled in the art with the attainment of some or all of the advantages of the embodiments. For example, according to various embodiments, a single component may be replaced by multiple components, and multiple components may be replaced by a single component, to perform a given function or functions. The described embodiments are therefore intended to cover all such modifications, alterations and adaptations without departing from the scope of the appended claims.

Various embodiments are directed to apparatuses, systems, and methods for the treatment of tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and illustrative. Variations and changes thereto may be made without departing from the scope of the claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

The entire disclosures of the following non-provisional United States patents are hereby incorporated by reference herein:

U.S. Pat. No. 7,381,209, entitled ELECTROSURGICAL INSTRUMENT;

U.S. Pat. No. 7,354,440, entitled ELECTROSURGICAL INSTRUMENT AND METHOD OF USE;

U.S. Pat. No. 7,311,709, entitled ELECTROSURGICAL INSTRUMENT AND METHOD OF USE;

U.S. Pat. No. 7,309,849, entitled POLYMER COMPOSITIONS EXHIBITING A PTC PROPERTY AND METHODS OF FABRICATION;

U.S. Pat. No. 7,220,951, entitled SURGICAL SEALING SURFACES AND METHODS OF USE;

U.S. Pat. No. 7,189,233, entitled ELECTROSURGICAL INSTRUMENT;

U.S. Pat. No. 7,186,253, entitled ELECTROSURGICAL JAW STRUCTURE FOR CONTROLLED ENERGY DELIVERY;

U.S. Pat. No. 7,169,146, entitled ELECTROSURGICAL PROBE AND METHOD OF USE;

U.S. Pat. No. 7,125,409, entitled ELECTROSURGICAL WORKING END FOR CONTROLLED ENERGY DELIVERY;

U.S. Pat. No. 7,112,201, entitled ELECTROSURGICAL INSTRUMENT AND METHOD OF USE;

U.S. Patent Application Publication No. 2010/0010299, entitled ENDOSCOPIC TRANSLUMENAL ARTICULATABLE STEERABLE OVERTUBE; and U.S. Patent Application Publication No. 2006/0111735, entitled CLOSING ASSEMBLIES FOR CLAMPING DEVICE.

Any patent, publication, or other disclosure material, in whole or in part, that is said to be incorporated by reference herein is incorporated herein only to the extent that the incorporated material does not conflict with existing definitions, statements or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The devices disclosed herein may be designed to be disposed of after a single use, or they may be designed to be used multiple times. In either case, however, the device may be reconditioned for reuse after at least one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of this application.

Preferably, the embodiments described herein will be processed before surgery. First a new or used instrument is obtained and, if necessary, cleaned. The instrument may then be sterilized. In one sterilization technique, the instrument is placed in a closed and sealed container, such as a plastic or TYVEK® bag. The container and instrument are then placed in a field of radiation that may penetrate the container, such as gamma radiation, x-rays, or higher energy electrons. The radiation kills bacteria on the instrument and in the container. The sterilized instrument may then be stored in the sterile container. The sealed container keeps the instrument sterile until it is opened in the medical facility.

The embodiments are not to be construed as limited to the particular embodiments disclosed. The embodiments are therefore to be regarded as illustrative rather than restrictive. Variations and changes may be made by others without departing from the scope of the claims. Accordingly, it is expressly intended that all such equivalents, variations and changes that fall within the scope of the claims be embraced thereby.

In summary, numerous benefits have been described which result from employing the embodiments described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical applications to thereby enable one of ordinary skill in the art to utilize the various embodiments and with various modifications as are suited to the particular use contemplated. It is intended that the claims submitted herewith define the overall scope.

What is claimed is:

1. A surgical instrument comprising:
    a handle;
    a shaft coupled to the handle and extending distally along a longitudinal axis;
    an end effector positioned at a distal portion of the shaft, wherein the end effector comprises:
        a first jaw member defining a first longitudinal slot and comprising a first pulley positioned at a distal portion of the first jaw member;
        a second jaw member defining a second longitudinal slot, wherein the second jaw member is pivotable towards the first jaw member;
        a reciprocating member translatable distally and proximally parallel to the longitudinal axis, and wherein the reciprocating member comprises:
            a transverse member positioned to pass through the first and second longitudinal slots as the reciprocating member translates distally and proximally;
            at least one flange positioned on a distal portion of the reciprocating member to exert a force tending to close the first and second jaw members when the transverse member passes through the first and second longitudinal slots; and
            a distal leading edge that defines a blade; and
        a cable extending distally from the handle through the shaft to the first pulley and proximally from the first pulley to the reciprocating member, such that proximally directed motion of the cable exerts a distally directed force on the reciprocating member.

2. The surgical instrument of claim 1, wherein the first jaw member is pivotable towards the second jaw member, wherein the second jaw member comprises a second pulley at a distal portion of the second jaw member and wherein the cable comprises:
    a first section extending distally to the first pulley and proximally from the first pulley to the reciprocating member; and
    a second section extending distally to the second pulley and proximally from the second pulley to the reciprocating member.

3. The surgical instrument of claim 2, wherein the first and second sections of the cable are joined at a splitter positioned proximal from the first and second jaw members.

4. The surgical instrument of claim 1, further comprising at least one pulley positioned proximal from the first and second jaw members and positioned to rout the cable.

5. The surgical instrument of claim 1, wherein the first pulley comprises at least one of a rotatable wheel a stationary peg and a rotatable peg.

6. The surgical instrument of claim 1, wherein the shaft comprises an articulation joint, wherein the articulation joint comprises a second pulley positioned to route the cable.

7. The surgical instrument of claim 1, wherein the at least one flange is positioned to translate distally and proximally within the first and second jaw members.

8. The surgical instrument of claim 1, wherein the at least one flange is positioned to translate distally and proximally outside the first and second jaw members.

9. The surgical instrument of claim 1, wherein the first jaw member further comprises a first electrode and the second jaw member further comprises a second electrode.

10. The surgical instrument of claim 9, wherein at least one of the first electrode and the second electrode comprises a first electrically conductive portion and a positive temperature coefficient (PTC) portion.

11. The surgical instrument of claim 10, wherein the PTC portion comprises at least one material selected from the group consisting of a polymer PTC material and a ceramic PTC material.

12. The surgical instrument of claim 9, wherein the PTC portion comprises a PTC material with a temperature dependent electrical resistance such that the electrical resistance of the PTC material increases to substantially eliminate current flowing through the PCT material at a predetermined temperature.

13. The surgical instrument of claim 9, further comprising an electrosurgical generator in electrical communication with the first and second electrodes.

14. The surgical instrument of claim 13, wherein the electrosurgical generator comprises feedback circuitry configured to modify power delivered to the first and second electrode based on at least one property of the electrode selected from the group consisting of tissue impedance and electrode temperature.

15. The surgical instrument of claim 1, wherein the first jaw member comprises a tissue engagement surface comprising a positive electrode and a negative electrode separated by an insulator.

16. The surgical instrument of claim 1, wherein the first jaw member is stationary.

17. A surgical instrument comprising:
a handle;
a shaft coupled to the handle and extending distally along a longitudinal axis;
an end effector positioned at a distal portion of the shaft, wherein the end effector comprises:
a first jaw member comprising a first pulley positioned at a distal portion of the first jaw member;
a second jaw member, wherein the second jaw member is pivotable towards the first jaw member; and
a translatable member translatable distally and proximally along the longitudinal axis, wherein distal translation of the translatable member exerts a force tending to pivot the second jaw member towards the first jaw member; and
a cable extending distally from the handle through the shaft to the first pulley and proximally from the first pulley to the translatable member, such that proximally directed motion of the cable exerts a distally directed force on the translatable member.

18. The surgical instrument of claim 17, wherein the first jaw member is stationary.

19. The surgical instrument of claim 17, wherein the first jaw member is pivotable towards the second jaw member, wherein the second jaw member comprises a second pulley at a distal portion of the second jaw member, and wherein the cable comprises:
a first section extending distally to the first pulley and proximally from the first pulley to the translatable member; and
a second section extending distally to the second pulley and proximally from the second pulley to the translatable member; and
wherein distal translation of the translatable member exerts a force tending to pivot the first jaw member towards the second jaw member.

20. The surgical instrument of claim 17, wherein the translatable member comprises a collar that is translatable distally and proximally from a pivot point of the second jaw member to a position distal from the pivot point of the second jaw member.

21. A surgical instrument comprising:
a handle;
a shaft coupled to the handle and extending distally along a longitudinal axis;
an end effector positioned at a distal portion of the shaft, wherein the end effector comprises:
a first jaw member defining a first longitudinal slot and comprising a first pulley positioned at a distal portion of the first jaw member;
a second jaw member defining a second longitudinal slot, wherein the second jaw member is pivotable towards the first jaw member;
a reciprocating member translatable distally and proximally along the longitudinal axis, and wherein the reciprocating member comprises:
a transverse member positioned to pass through the first and second longitudinal slots as the reciprocating member translates distally and proximally;
at least one flange positioned on a distal portion of the reciprocating member to exert a force tending to close the first and second jaw members when the transverse member passes through the first and second longitudinal slots; and
a distal leading edge that defines a blade; and
a cable extending distally from the handle through the shaft to the first pulley and proximally from the first pulley to the reciprocating member, such that proximally directed motion of the cable exerts a distally directed force on the reciprocating member.

* * * * *

UNITED STATES PATENT AND TRADEMARK OFFICE
CERTIFICATE OF CORRECTION

PATENT NO. : 8,623,044 B2  
APPLICATION NO. : 12/758284  
DATED : January 7, 2014  
INVENTOR(S) : Timm et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 768 days.

Signed and Sealed this  
Fourth Day of August, 2015

Michelle K. Lee  
*Director of the United States Patent and Trademark Office*